United States Patent [19]

Ciganek et al.

[11] Patent Number: 5,480,892

[45] Date of Patent: Jan. 2, 1996

[54] (N-PHTHALIMIDOALKYL)PIPERIDINES

[75] Inventors: Engelbert Ciganek, Kennett Square, Pa.; Sang W. Tam, Hockessin; Ann S. Wright, Wilmington, both of Del.

[73] Assignee: The Du Pont Merck Pharmaceutical Company, Wilmington, Del.

[21] Appl. No.: 298,268

[22] Filed: Aug. 31, 1994

Related U.S. Application Data

[60] Division of Ser. No. 876,542, Apr. 30, 1992, Pat. No. 5,356,906, which is a continuation-in-part of Ser. No. 602,024, Oct. 23, 1990, abandoned, which is a continuation-in-part of Ser. No. 428,097, Oct. 23, 1989, abandoned.

[51] Int. Cl.$^6$ .................. A61K 31/445; C07D 401/06
[52] U.S. Cl. .................. 514/323; 546/200; 546/201
[58] Field of Search .................. 546/200, 201; 514/323

[56] References Cited

U.S. PATENT DOCUMENTS 4,849,431  7/1989  Sugimoto et al. .................. 514/331

*Primary Examiner*—Jacqueline Haley

[57] ABSTRACT

There are described novel (N-phthalimidoalkyl) piperidine compounds which exhibit selective sigma-receptor antagonism and therefore are useful in the treatment of physiological or drug induced psychosis and dyskinesia in a mammal. Also described are pharmaceutical compositions containing sigma selective compounds and methods of using these compositions for treating physiological or drug induced psychosis or dyskinesia in a mammal. Further provided are methods for preparing the compounds of this invention.

21 Claims, No Drawings

(N-PHTHALIMIDOALKYL)PIPERIDINES

REFERENCE TO RELATED EARLIER FILED APPLICATIONS

This is a division of application Ser. No. 07/876,542, filed Apr. 30, 1992 now U.S. Pat. No. 5,356,906, which is a continuation-in-part of U.S. Ser. No. 07/602,024 filed Oct. 23, 1990 (now abandoned); which was a continuation-in-part of U.S. Ser. No. 07/428,097 filed Oct. 23, 1989 (now abandoned).

FIELD OF THE INVENTION

This invention relates to novel (N-phthalimidoalkyl) piperidine compounds, pharmaceutical compositions containing them and methods of using these compounds and compositions to treat physiological or drug induced psychoses in mammals and also as antidyskinetic agents.

BACKGROUND OF THE INVENTION

U.S. Pat. No. 4,849,431 (Sugimoto et al.) discloses compounds of the formula:

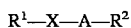

wherein:

$R^1$ denotes a univalent group derived from one selected among substituted or unsubstituted benzene, pyridine, pyrazine, indole, anthraquinone, quinoline, substituted or unsubstituted phthalimide
including specifically:

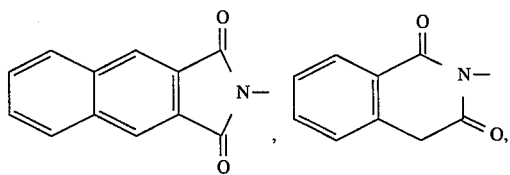

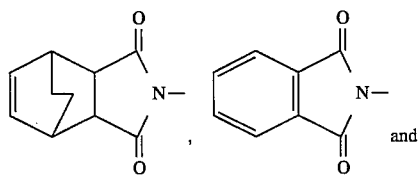

pyridinecarboxylic acid imide, pyridine N-oxide, pyrazinedicarboxylic acid imide, substituted or unsubstituted quinazolinedione and pyromerylimide;

X denotes a group of the formula $-(CH_2)_n-$, $-O(CH_2)_n-$, $-S(CH_2)_n-$, $-NH(CH_2)_n-$, $-SO_2NH(CH_2)_n-$, $-NH-C(=O)-(CH_2)_n-$, $-NH(CH_2)_n-C(=O)-$, $-C(=O)-O(CH_2)_n-$, $-CH_2NH(CH_2)_n-$, $-C(=O)-N(R^3)-(CH_2)_n$, or $-OCH_2-CH(OH)-CH_2-$ (in all the above formulas, n is an integer of 1 through 7 and $R^3$ represents a lower alkyl group or a benzyl group);

ring A denotes a group of the formula,

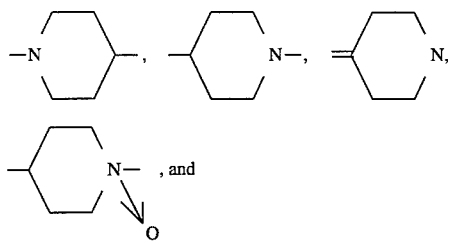

$R^2$ denotes hydrogen, lower alkyl, substituted or unsubstituted benzyl, substituted or unsubstituted benzoyl, pyridyl, 2-hydroxyethyl, pyridylmethyl or a group of the formula

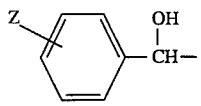

(wherein Z represents a halogen atom).

These compounds are disclosed as being useful in the treatment and prevention of dementia and sequelae of cerebrovascular disease.

U.S. Pat. No. 4,495,194 and U.S. Pat. No. 4,600,758 describe 3-oxoisoindole derivatives having antihypertensive and/or diuretic properties characterized by a compound of the formula:

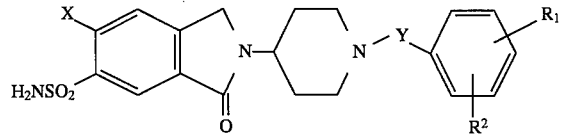

wherein:

X is halogen or trifluoromethyl;

$R^1$ and $R^2$ are independently hydrogen, lower alkyl, lower alkoxy, lower alkenyloxy, lower alkylthio, trifluoromethyl, cyano, or nitro;

Y is a single bond or a divalent straight or branched chain alkylene radical of 1 to 4 carbon atoms inclusive.

U.S. Pat. No. 4,495,194 and U.S. Pat. No. 4,600,758 also describe the following compounds as intermediates:

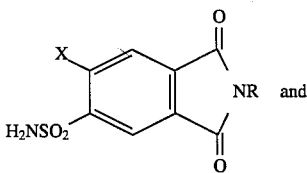

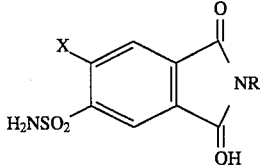

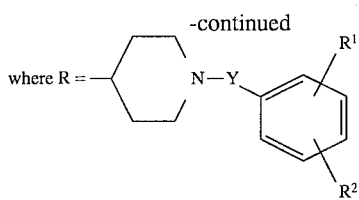

GB 1,425,578 discloses compounds of the formula:

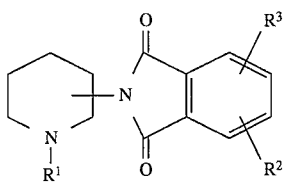

and their pharmaceutically acceptable acid addition salts, wherein:

$R^1$ is hydrogen, alkyl, aralkyl or alkyl substituted by a heterocyclyl group;

$R^2$ and $R^3$, which may be the same or different, are hydrogen, halogen, trifluoromethyl, lower alkyl, lower alkoxy, nitro, hydroxy, amino, monoalkylamino or dialkylamino.

These compounds are disclosed as having anti-convulsant activity and in some cases, anti-inflammatory activity or anti-arrhythmic activity.

U.S. Pat. No. 4,289,781 (Bengtson et al.) describes compounds useful for the treatment of psychoses in man such compounds having the formula:

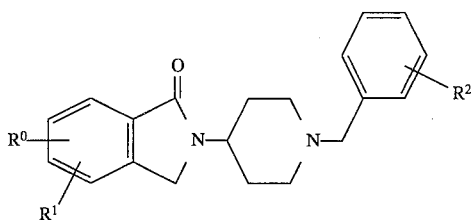

wherein:

$R^0$ and $R^1$ are the same or different and are each selected from hydrogen, halogen, alkyl having 1, 2 or 3 carbon atoms, alkoxy having 1, 2, or 3 carbon atoms, and trifluoromethyl; and $R^2$ is selected from hydrogen, halogen, alkyl having 1, 2, or 3 carbon atoms, alkoxy having 1, 2, or 3 carbon atoms, and trifluoromethyl.

The compounds described in the prior art, cited above, do not show the sigma receptor selectivity demonstrated by the compounds of the present invention. It is this sigma receptor selectivity which makes the compounds of the present invention advantageous over compounds of the prior art. Traditionally, antipsychotic agents have been potent dopamine receptor antagonists. For example, phenothiazines such as chlorpromazine and most butyrophenones such as haloperidol are potent dopamine receptor antagonists. These dopamine receptor antagonists are associated with a high incidence of side effects, particularly Parkinson-like motor effects or extra-pyramidal side-effects (EPS), and dyskinesias including tardive dyskinesias at high doses. Many of these side effects are not reversible even after the dopamine receptor antagonist agent is discontinued.

The present invention is related to antipsychotic agents which are selective antagonists for the sigma receptor. Unlike dopamine receptor blockers known in the art, the compounds of the present invention have low potential for the typical movement disorder side-effects associated with the dopamine antagonist antipsychotic agents while they maintain the ability to antagonize aggressive behavior and antagonize hallucinogenic-induced behavior.

DETAILED DESCRIPTION OF THE INVENTION

The sigma-selective antipsychotic compounds of the present invention are (N-phthalimidoalkyl) piperidines of the formula:

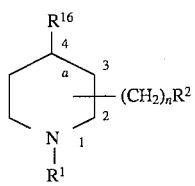

(I)

or a pharmaceutically acceptable salt or an N-oxide thereof wherein:

a is a single or double bond, provided that when a is a double bond then $R^2(CH_2)_n$ is attached at the C—4 position of the piperidine ring and $R^{16}$ is not present;

n is 0–4, provided that when $(CH_2)_nR^2$ is attached to the C—2 position of the piperidine ring then n is 2–4;

$R^1$ is $(CH_2)_mR^3$ or $(CH_2)_pAr$, where m is 1–4 and p is 1–4;

$R^2$ is

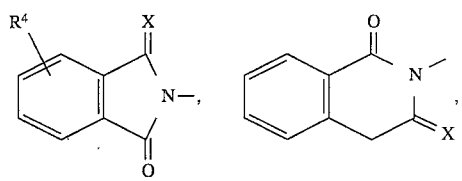

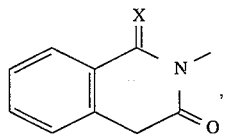

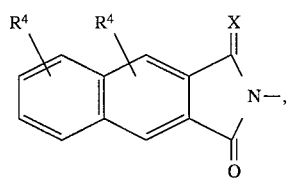

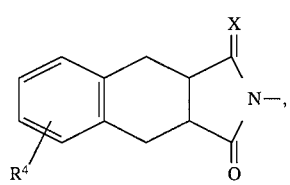

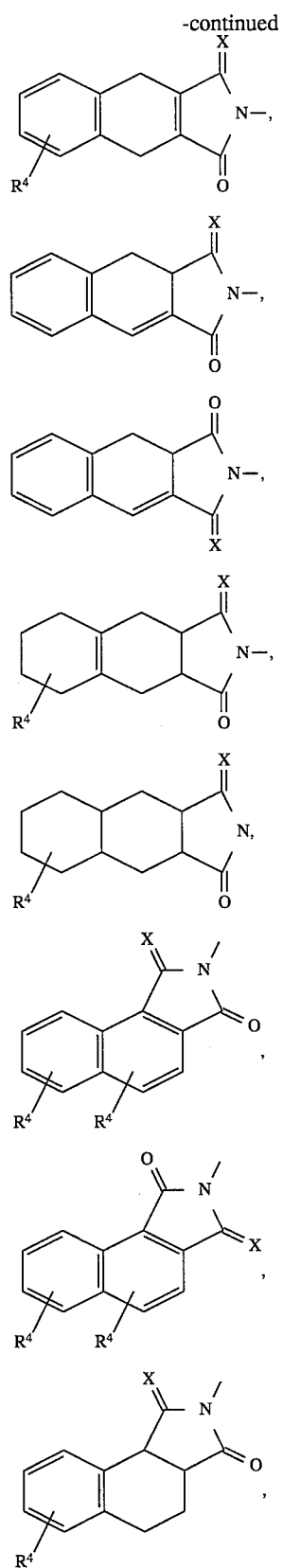
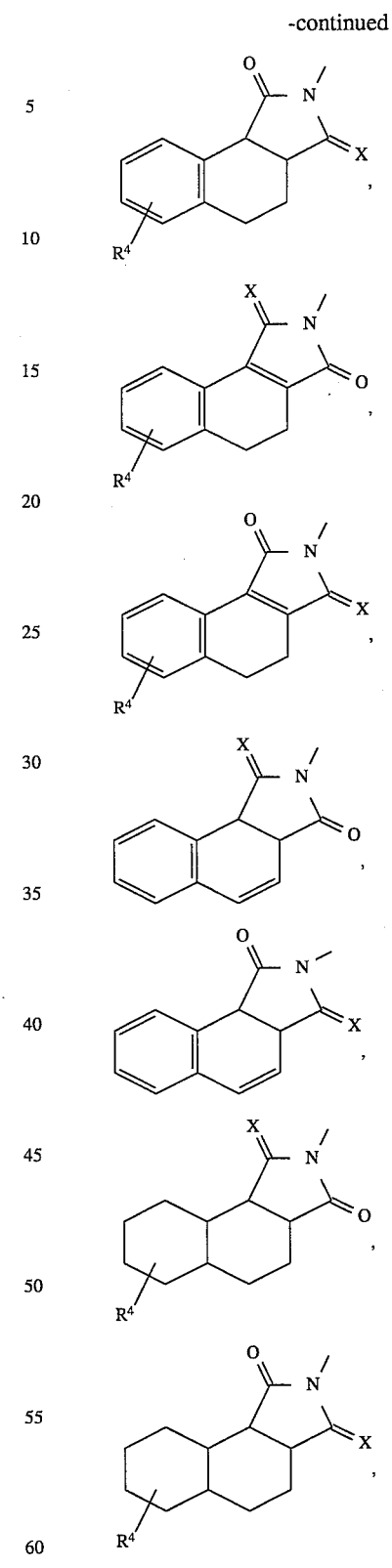

-continued

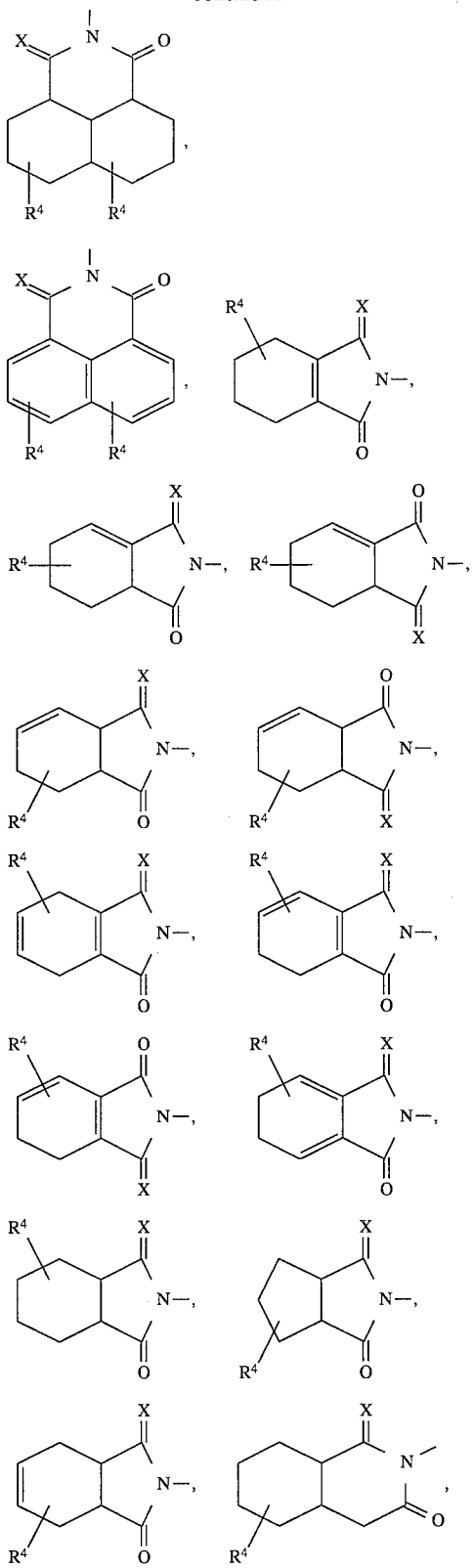

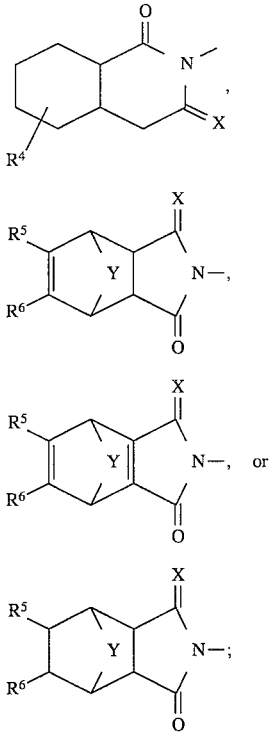

$R^3$ is cycloalkyl of 3 to 8 carbon atoms;

$R^4$ is 1–4 substituents independently selected from the group consisting of H, halogen, $NO_2$, $NH_2$, haloalkyl of 1 to 3 carbon atoms and 1 to 7 halogen atoms, $C_1$–$C_3$ alkyl, $NHCOR^7$, NHCO-phenyl, OH, $OR^8$ and Ar';

$R^5$ and $R^6$ independently are H, alkyl of 1 to 3 carbon atoms, Ar" or taken together form a 2–5 carbon atom alkyl or alkenyl group, such as —CH=CH—CH=CH—;

$R^7$ and $R^8$ independently are H or alkyl of 1 to 3 carbon atoms;

X is O (carbonyl); ($H_2$); (H, OH); ($R^9$, OH); (Ar''', OH); (H, $R^9$); or (H, $OR^{10}$); wherein, for example, the designation (H, OH) indicates that H and ,OH are connected by single bonds to the carbon atom of $R^2$ which is shown above to be connected to X by a double bond;

Y is $CH_2$, $CHR^{10}$, $C(R^{10})_2$, O, $CH_2CH_2$, $(CH_2)_3$,

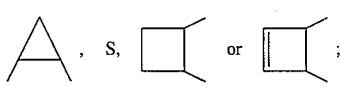, S, ☐ or ☐ ;

Ar, Ar', Ar" and Ar''' independently are phenyl, naphthyl, pyridyl, pyrimidyl, quinolyl, or isoquinolyl, each optionally substituted with 1–5 substituents independently selected from the group consisting of:
H, halogen, OH, alkoxy of 1 to 3 carbon atoms, $NR^{11}R^{12}$, SH, $S(O)_tR^{13}$, where t is 0—2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, or phenyl;

$R^9$ is selected from the group consisting of:
  alkyl of 1–20 carbon atoms or alkenyl or alkynyl of 2–20 carbon atoms, said alkyl, alkenyl, or alkynyl group being optionally substituted with substituents independently selected from:
    1–2 cycloalkyl groups of 3–8 carbons,
    1–6 halogen,
    1–3 OH,
    1–3 $OR^{10}$,
    1–2 Ar'''';
  cycloalkyl of 3–8 carbon atoms; or
  Ar'''';

$R^{10}$ is alkyl of 1–3 carbon atoms;

Ar'''' is phenyl, naphthyl, pyrrolyl, furyl, thienyl, indolyl, benzofuryl, benzothienyl, pyridyl, pyrimidyl, quinolyl, or isoquinolyl, each of which may be substituted with 0–5 groups independently selected from the group consisting of:
  H, halogen, OH, alkoxy of 1 to 3 carbon atoms, $NR^{11}R^{12}$, SH, $S(O)_tR^{13}$, where t is 0–2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, or phenyl;

$R^{11}$–$R^{15}$ independently are H or alkyl of 1 to 3 carbon atoms;

$R^{16}$ is H; OH; O-alkyl of 1–6 carbons; O-acyl of 1–8 carbons; alkyl of 1–12 carbons; phenyl or 1- and 2-naphthyl optionally substituted with one or two substituents independently selected from the group consisting of:
  F, Cl, Br, I, alkyl, phenyl, perfluoroalkyl, alkoxy, aryloxy, alkylthio, arylthio, perfluoroalkoxy, perfluoroalkylthio, dialkylamino (where alkyl and alkoxy are from 1–12 carbons and aryl is from 6–12 carbons);
  or 2- and 3- pyrrolyl; 2- and 3- furyl; 2- and 3-thienyl; 2,3, and 4-pyridyl; 2- and 3-benzofuryl; 2- and 3-indolyl; 2- and 3- benzothienyl; 2, 3, and 4- quinolyl; and 1, 3, and 4-isoquinolyl;

with the following provisos:
  (1) if n is O and $R^2$ is attached at the C-4 position of the piperidine ring,
    then $R^2$ cannot be:

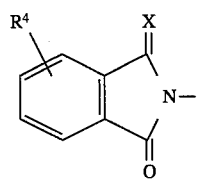

if X is O; $H_2$; or H, OH;
where there are two $R^4$ substituents and one is $H_2NSO_2$ and the other is halogen or $CF_3$;

(2) if $R^1$ is $(CH_2)_pAr$ and p is 1 and $—(CH_2)_nR^2$ (n=1 to 7) is attached at the C-4 position of the piperidine ring,
    then $R^2$ cannot be:

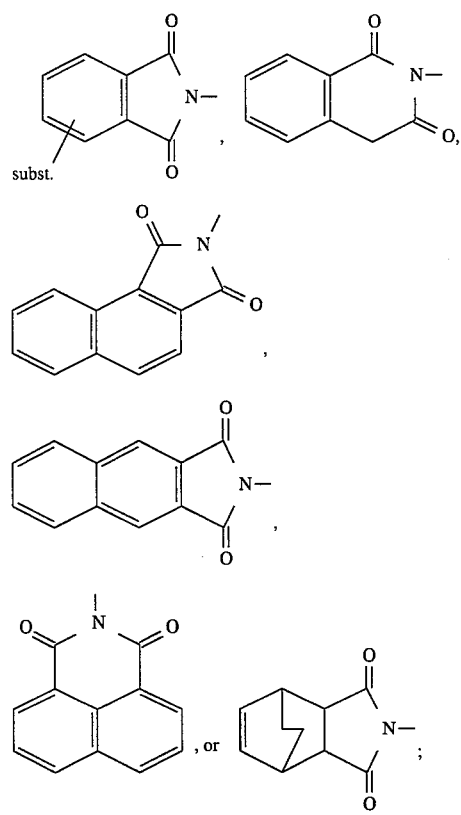

(3) if $R^1$ is $(CH_2)_pAr$ (where p is 1);

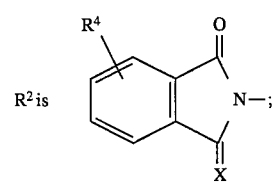

$R^4$ is H, alkyl, $CF_3$, halogen or alkoxy;
$(CH_2)_nR^2$, (n=O), is attached at the C-4 position on the piperidine ring;
then X cannot be $H_2$ or O.

(4) if $R^1$ is $(CH_2)_pAr$ (p is >0); $R^2$ is attached at the C-3 or C-4 position of the piperdine ring; and

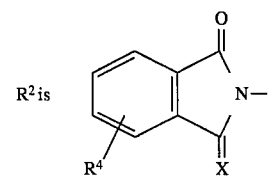

(where $R^4$ is H, halogen, $CF_3$, alkyl, alkoxy, $NH_2$, alkylamino and dialkylamino);
then X cannot be O; and (5) when $(CH_2)_n R_2$ is attached to the 4-position of the piperidine ring, then $R^{16}$ is H, OH, alkyl or aryl.

Some compounds of the present invention can exist as optical isomers and both the racemic mixtures of these isomers as well as the individual optical isomers which confer activity are within the scope of the present invention. The racemic mixtures can be separated into their individual isomers by techniques well known to those skilled in the art.

In addition some compounds of the present invention can exist as cis or trans isomers and although these are not all specifically set forth, the cis and trans fused compounds as known to those skilled in the art, are within the scope of this invention.

Preferred compounds of the present invention are compounds of formula (I) wherein:

n is 1–4; and/or
$R^1$ is $(CH_2)_p Ar$; and/or
p is 1–2; and/or
$R^2$ is

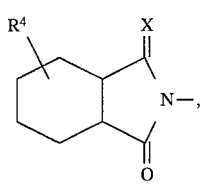 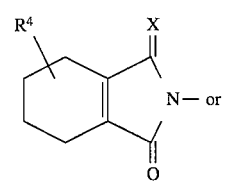

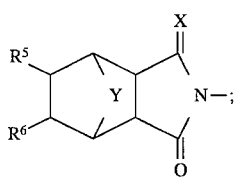

and/or $(CH_2)_n R^2$ is attached at the C-4 position of the piperidine ring; and/or X is O, $H_2$, or $(H, R^9)$, and $R^9$ is alkyl of 1–8 carbon atoms; and/or $R^4$, $R^5$ and $R^6$ are all H; and/or Ar is phenyl; and/or Y is $(CH_2)_3$ or O.

More preferred compounds of the present invention are the compounds of formula (I) wherein n is 1.

Specifically preferred compounds are compounds of formula (I) wherein:

(1) $(CH_2)_n R^2$ is attached at the C-4 position of the piperidine ring;
n is 1;
$R^2$ is

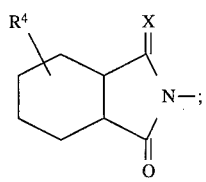

X is O;
$R^4$ is H;
$R^1$ is $(CH_2)_p Ar$;
p is 2; and
Ar is phenyl.

(2) $(CH_2)_n R^2$ is attached at the C-4 position of the piperidine ring;
n is 1;
$R^2$ is

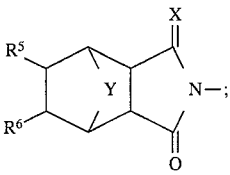

X is O;
Y is $(CH_2)_3$ and $R^5$ and $R^6$ are H;
$R^1$ is $(CH_2)_p Ar$;
p is 2; and
Ar is phenyl.

(3) $(CH_2)_n R^2$ is attached at the C-4 position of the piperidine ring;
n is 1;
$R^2$ is

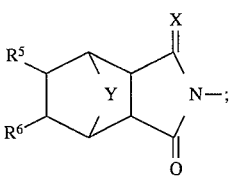

X is O;
Y is O;
$R^5$ and $R^6$ are H;
$R^1$ is $(CH_2)_p Ar$;
p is 2; and
Ar is phenyl.

(4) $(CH_2)_n R^2$ is attached at the C-4 position of the piperidine ring;
n is 1;
$R^2$ is

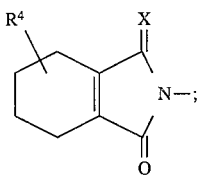

X is $H_2$, $(H,R^9)$ and $R^9$ is alkyl of 1–8 carbon atoms;
$R^4$ is H;
$R^1$ is $(CH_2)_p Ar$;
p is 2; and
Ar is phenyl.

Also provided are pharmaceutical compositions and methods of using them for the treatment of physiological or drug induced psychosis or dyskinesia in a mammal, said compositions comprising a pharmaceutically acceptable carrier and an antipsychotic or an antidyskinetic effective amount of a compound having the formula (I):

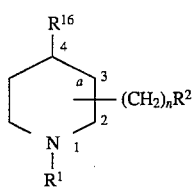
(I)
or a pharmaceutically acceptable salt or an N-oxide thereof wherein:
a is a single or double bond, provided that when a is a double bond, then $R^2(CH^2)_n$ is attached at C-4 and $R^{16}$ does not apply;
n is 0–4, provided that when $(CH_2)_nR^2$ is attached to the 2-position of the piperidine ring then n is 2–4;
$R^1$ is $(CH_2)_mR^3$ or $(CH_2)_pAr$, where m is 1–4 and p is 1–4;
$R^2$ is
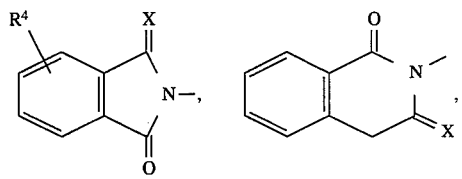
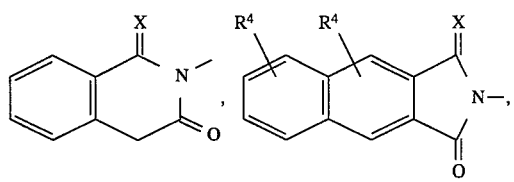
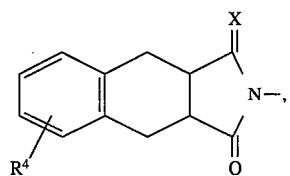
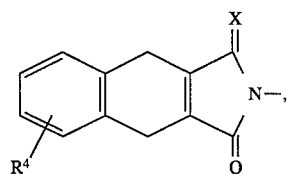
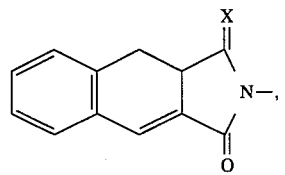
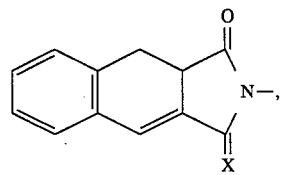
-continued
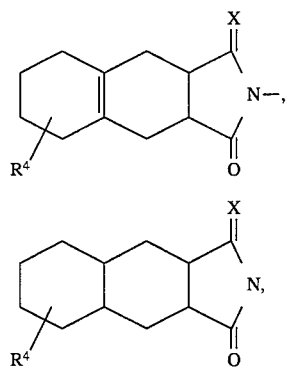
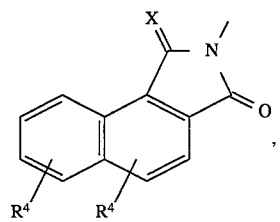
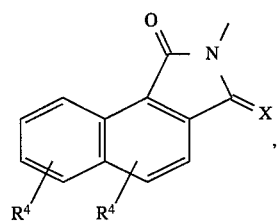
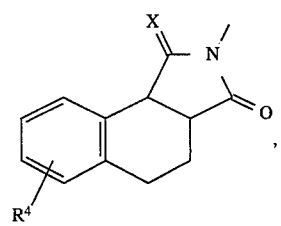
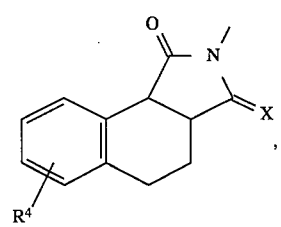
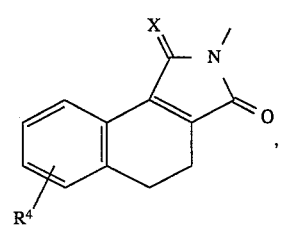

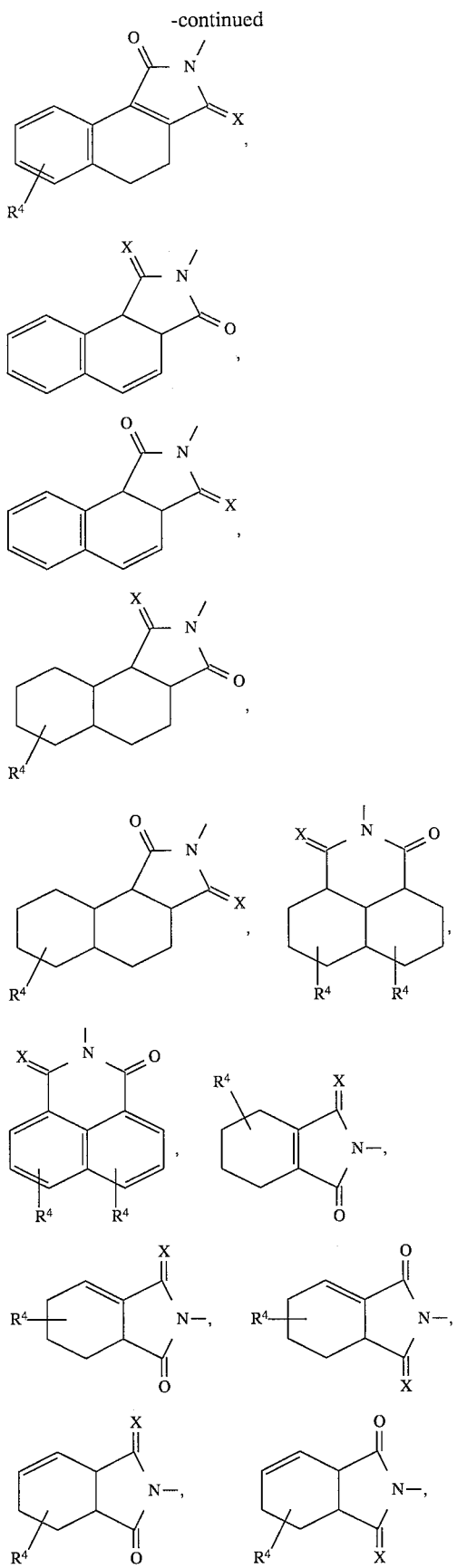
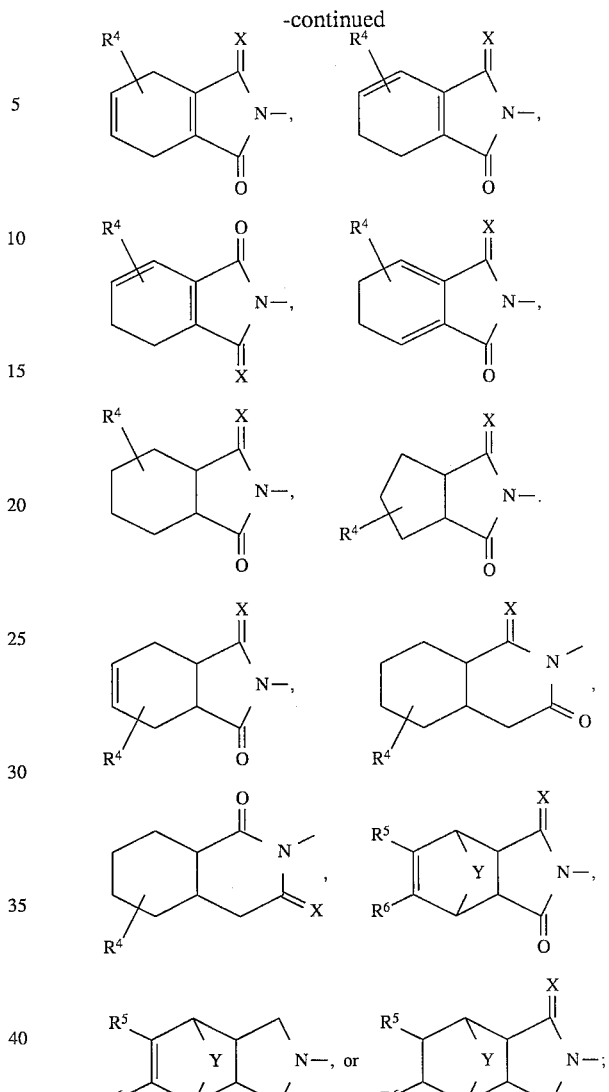

$R^3$ is cycloalkyl of 3 to 8 carbon atoms;

$R^4$ is 1-4 substituents independently selected from the group consisting of H, halogen, $NO_2$, $NH_2$, haloalkyl of 1 to 3 carbon atoms and 1 to 7 halogen atoms, $C_1$–$C_3$ alkyl, $NHCOR^7$, NHCO-phenyl, OH, $OR^8$ and Ar';

$R^5$ and $R^6$ independently are H, alkyl of 1 to 3 carbon atoms, Ar" or taken together form a 2-5 carbon atom alkyl or alkenyl group, such as —CH=CH—CH=CH—;

$R^7$ and $R^8$ independently are H or alkyl of 1 to 3 carbon atoms;

X is O; $H_2$; (H, OH); ($R^9$, OH); (A'", OH); (H, $R^9$); or (H, $OR^{10}$);

Y is $CH_2$, $CHR^{10}$, $C(R^{10})_2$, O, $CH_2CH_2$, $(CH_2)_3$,

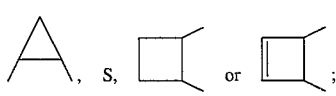, S, ☐ or ☐;

Ar, Ar', Ar" and Ar"' independently are phenyl, naphthyl, pyridyl, pyrimidyl, quinolyl, or isoquinolyl, each optionally substituted with 1–5 substituents independently selected from the group consisting of:
H, halogen, OH, alkoxy of 1 to 3 carbon atoms, $NR^{11}R^{12}$, SH, $S(O)_tR^{13}$, where t is 0–2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, or phenyl;

$R^9$ is selected from the group consisting of:
alkyl of 1–20 carbon atoms or alkenyl or alkynyl of 2–20 carbon atoms, said alkyl, alkenyl, or alkynyl group being optionally substituted with substituents independently selected from:
1–2 cycloalkyl groups of 3–8 carbons,
1–6 halogen,
1–3 OH,
1–3 $OR^{10}$,
1–2 Ar"";
cycloalkyl of 3–8 carbon atoms; or
Ar"";

$R^{10}$ is alkyl of 1–3 carbon atoms;

Ar"" is phenyl, naphthyl, pyrrolyl, furyl, thienyl, indolyl, benzofuryl, benzothienyl, pyridyl, pyrimidyl, quinolyl, or isoquinolyl, each of which may be substituted with 0–5 groups independently selected from, the group consisting of:
H, halogen, OH, alkoxy of 1 to 3 carbon atoms, $NR^{11}R^{12}$, SH, $S(O)_tR^{13}$, where t is 0–2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, or phenyl;

$R^{11}$–$R^{15}$ independently are H or alkyl of 1 to 3 carbon atoms; and $R^{16}$ is H; OH; O-alkyl of 1–6 carbons; O-acyl of 1–8 carbons; alkyl of 1–12 carbons; phenyl or 1- and 2-naphthyl optionally substituted with one or two substituents independently selected from the group consisting of:
F, Cl, Br, I, alkyl, phenyl, perfluoroalkyl, alkoxy, aryloxy, alkylthio, arylthio, perfluoroalkoxy, perfluoroalkylthio, and dialkylamino (where alkyl and alkoxy are from 1–12 carbons and aryl is from 6–12 carbons);
or 2- and 3- pyrrolyl; 2- and 3- furyl; 2- and 3-thienyl; 2,3, and 4-pyridyl; 2- and 3- benzofuryl; 2- and 3-indolyl; 2- and 3- benzothienyl; 2, 3, and 4- quinolyl; and 1, 3, and 4-isoquinolyl;

with the following provisos:
(1) when $R^1$ is $(CH_2)_pAr$ (p is 1);
$R^2$ is

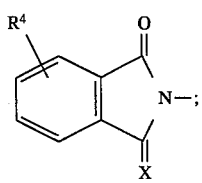

and
$(CH_2)_nR^2$, (n=0), is attached at the C-4 position on the piperidine ring;
then X cannot be $H_2$; and (2) when $(CH_2)_nR^2$ is attached to the 4-position of the piperidine ring, then $R^{16}$ is H, OH, alkyl or aryl.

Also provided in the present invention is a process for preparing the compounds of Formula (I) described above comprising:
(a) reacting a pyridinylalkylamine of the formula:

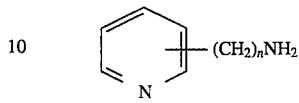

(n is 0–4) with an anhydride corresponding to $R^2$ (where N- is replaced by O) such as

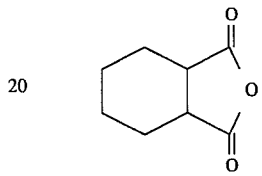

to yield imides of the formula:

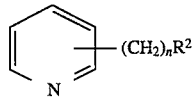

(where n and $R^2$ are as defined in claim 1 and X=O);

(b) reacting the imides of step (a) with alkylating agents of the formula:
$R^1Z$ (where Z is Cl, Br, I or an activated ester group) in an appropriate solvent at temperatures between about 0°–200° C. to yield quaternary pyridinium salts of the formula:

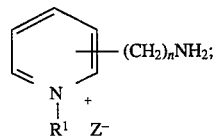

and (c) reducing the $Z^-$ salts of step (b) to the compounds of claim 1 by catalytic hydrogenation in an appropriate solvent and optionally in the presence of an appropriate acid.

In the present invention it has been discovered that the compounds above are useful as agents to treat physiological or drug induced psychosis and as antidyskenetic agents. Also provided are pharmaceutical compositions containing compounds of Formula (I) as described above.

The present invention also provides methods for the treatment of drug induced psychosis or dyskinesia by administering to a host suffering from such drug induced psychosis or dyskinesia a pharmaceutically effective amount of a compound of Formula (I) as described above.

The compounds herein described may have asymmetric centers. All chiral, enantiomeric, diastereomeric, and racemic forms are included in the present invention. Thus, the compounds of Formula (I) may be provided in the form of an individual stereoisomer, a non-racemic stereoisomer mixture, or a racemic mixture.

Many geometric isomers of olefins, C=N double bonds, and the like can also be present in the compounds described herein, and all such stable isomers are contemplated in the present invention.

When any variable occurs more than one time in any constituent or in Formula (I), or any other formula herein, its definition on each occurrence is independent of its definition at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms. The number of carbon atoms in a group is specified herein, for example, as $C_1$–$C_5$ to indicate 1–5 carbon atoms. As used herein "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like. "Cycloalkylalkyl" is intended to include cycloalkyl attached to alkyl. "Halo" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; "carbocyclic" is intended to mean any stable 5- to 7- membered monocyclic or bicyclic or 7- to 14-membered bicyclic or tricyclic carbon ring, any of which may be saturated, partially unsaturated, or aromatic, for example, indanyl or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, pyrazinyl, quinazzoyl, phthalazinyl, naphthyridinyl or octahydroisoquinolinyl.

The term "substituted", as used herein, means that one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive to a useful degree of purity from a reaction mixture, and formulation into an efficacious therapeutic agent.

As used herein, "pharmaceutically acceptable salts" refer to derivatives of the disclosed compounds that are modified by making acid or base salts. Examples include, but are not limited to, mineral or organic acid salts of basic residues such as amines; alkali or organic salts of acidic residues such as carboxylic acids.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Synthesis

Compounds of formula (I) may be made by various methods set forth herein.

Method A

The reaction of amines of type 1 with the anhydrides corresponding to $R^2$ (in which N- is replaced by O) in solvents such as tetrahydrofuran, toluene, or dimethylformamide at temperatures of about 0°–100° C. gives amide acid intermediates of type 2. These can be converted into the compounds of formula (I), of this invention, by a number of methods including: heating to about 100°–250° C. in a high-boiling solvent such as dimethylformamide, xylene, or 2-methoxyethyl ether; treatment with an acid chloride such as acetyl chloride at temperatures of about 25°–100° C.; or treatment with anhydrides such as acetic anhydride, optionally in the presence of a base such as sodium acetate, temperatures of about 50°–200° C. This method, which can be used to prepare the compounds of this invention where X=O, is illustrated by the following Scheme:

Scheme A

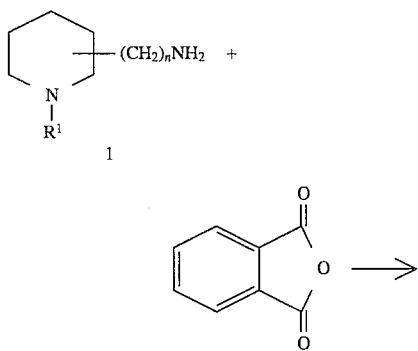

-continued
Scheme A

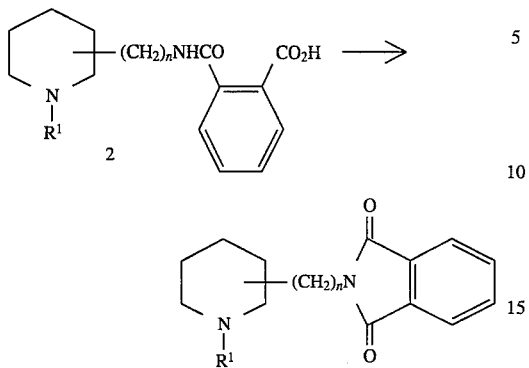

Alternatively, the two reactions of Scheme A may be carried out in a single step by heating amines 1 with anhydrides corresponding to $R_2$ (where N- is replaced by O) in high-boiling solvents, such as dimethylformamide or ethylene glycol dimethyl ether, or without solvents to temperatures of about 140° to 200°.

The amines 1 and the anhydrides corresponding to $R^2$ where N- is replaced by O are known in the literature or can be prepared by standard methods: Harper, N. J., Chignell, C. F.; *J. Med. Chem.* 1964, 7, 729; Abou-Gharbia, M., et al., ibid., 1988, 31, 1382.

Method B

In a variation of Method A, amines 1 are replaced by the corresponding pyridine derivatives 3. Preparation of the imides of type 4 is carried out in the same way as described in Method A. The intermediates of type 4 are then reacted with an alkylating agent of type $R^1Z$, where Z is Cl, Br, I or an activated ester group such as $OSO_2$-alkyl or $OSO_2$- aryl, at temperatures of about 0° to 200° C. in solvents such as ether, tetrahydrofuran, acetonitrile, alcohols such as ethanol or n-butanol, or dimethylformamide. The quaternary pyridinium salts of type 5 so obtained are then reduced to the compounds of the invention by treatment with hydrogen in the presence of a catalyst such as platinum at temperatures of about 0° to 200° C. and hydrogen pressures of 1–100 atm. in solvents such as acetic acid or ethanol optionally in the presence of an acid such as hydrochloric acid. This method, which can be used to prepare compounds of this invention where X=O that do not contain functionalities that are reduced under the conditions of the catalytic hydrogenation, is illustrated by the following Scheme:

Scheme B

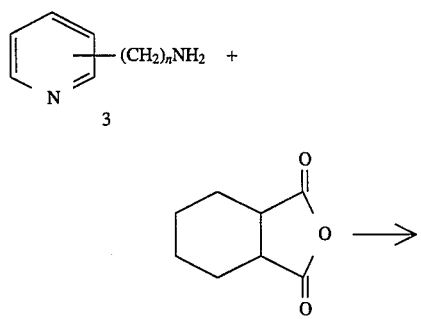

-continued
Scheme B

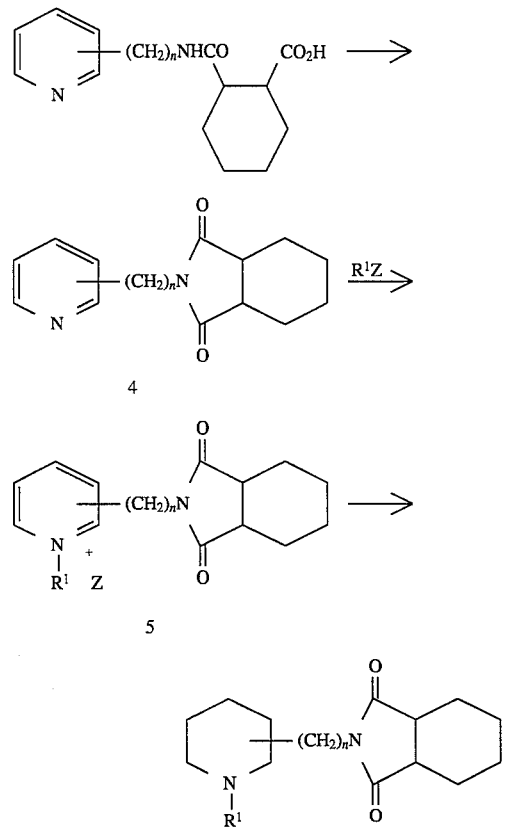

Amines 3 are known in the literature or can be prepared by standard methods: Satoh, T. and Suzuki, S., *Tetrahedron Lett.*, 1969, 4555.

Method C

Imides, $R^2H$, are treated with a base, such as sodium hydride or potassium hydride in aprotic solvents such as tetrahydrofuran, dimethylformamide or dimethylsulfoxide at temperatures of about 0° to 100° C. to give salts of type 6. The salts are then reacted with pyridine derivatives of type 7 where Z is Cl, Br, I or an activated ester such as $OSO_2$-alkyl or $OSO_2$-aryl in the same solvents at temperatures of about 0° to 150° C. to give intermediates of type 8. These are then treated with an alkylating agent $R^1Z$ and the quaternary pyridinium salts so obtained are reduced to the compounds of this invention as described in Method B. This method, which can be used to prepare compounds of this invention where n=1–4, X=O; $H_2$; $H,R^9$; $H,OR^9$ and that do not contain groups that are reduced under the conditions of the catalytic hydrogenation, is illustrated by the following scheme:

Scheme C

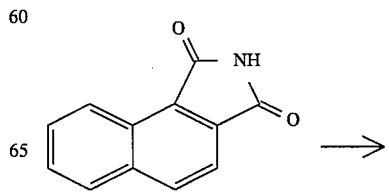

-continued
Scheme C

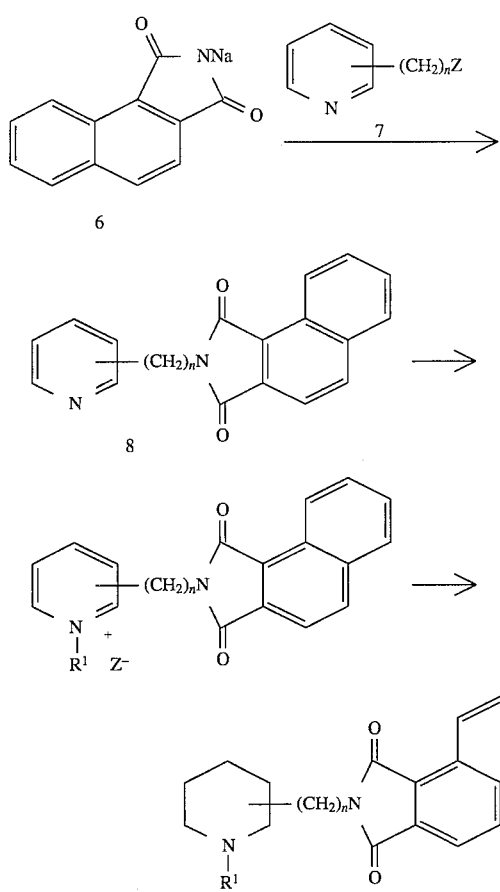

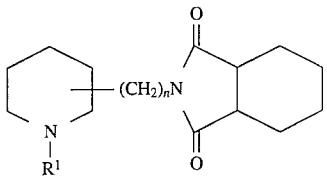

-continued
Scheme C-1

The imides $R^2H$ are known in the literature or can be prepared from the corresponding anhydrides by methods well known in the literature: Kitahonoki, K; Kakehi, M., U.S. Pat. No. 3,126,395 (1964).

Method D

Amines of type 1 (as specified in Method A) are allowed to react with maleic anhydride or maleic anhydrides substituted with one or two $R^4$ groups to give maleamic acids of type 10. The latter are converted into the maleimides of type 11 by well-known methods such as those given in Method A. The maleimides of type 11 are then subjected to the Diels-Alder reaction with dienes listed below which are optionally substituted with $R^5$ and $R^6$ in solvents such as tetrahydrofuran, acetonitrile, or aromatic hydrocarbons such as toluene or xylene, or chlorinated aromatic hydrocarbons such as chlorobenzene or dichlorobenzene; at temperatures of 0°–250° C. and pressures of 1–15,000 atm. to give certain compounds of this invention. The Diels-Alder reaction is optionally carried out in the presence of a radical inhibitor such as hydroquinone or phenothiazine to prevent polymerization of the dienes.

In a variation of this Method C, salts of type 6 are reacted with alkylating agents of type 9 where Z is as defined above under the same conditions is described above to give the compounds of this invention where n=0–4 and X=O; $H_2$; $H,R^9$ or $H,OR^9$, as illustrated by the following scheme:

Scheme C-1

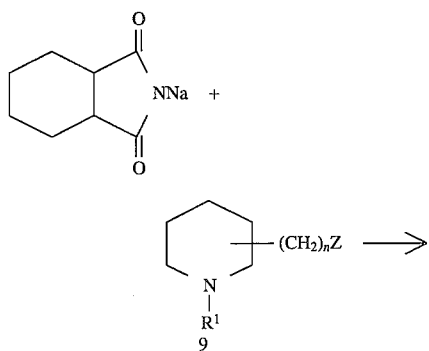

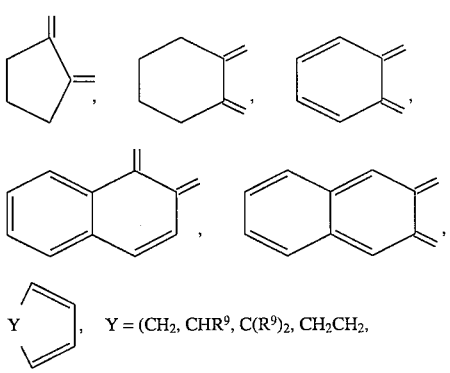

$Y = (CH_2, CHR^9, C(R^9)_2, CH_2CH_2,$
$(CH_2)_3, O, S)$

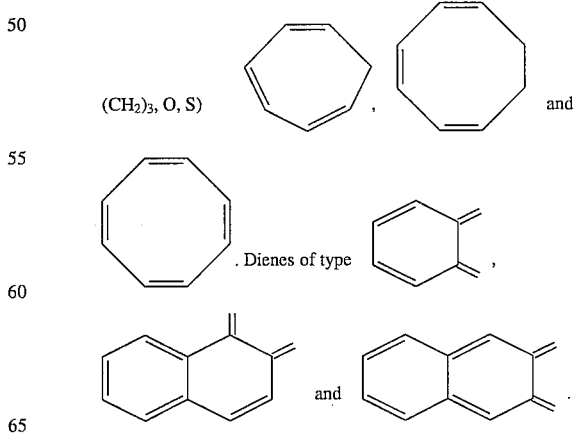

and . Dienes of type are obtained in situ by methods well known in the literature, for instance by heating compounds of type

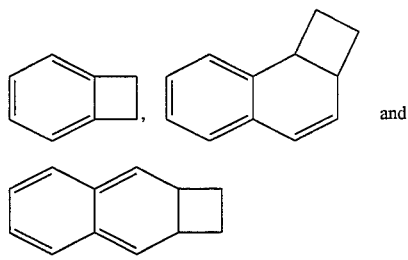

respectively to temperatures of about 60°–200° C. Dienes of type

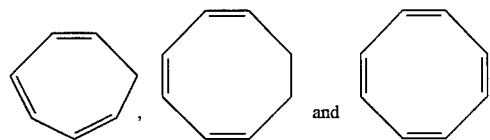

are known to undergo the Diels-Alder reaction in the form of their valence isomers

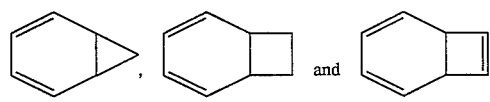

respectively to give compounds of this invention where Y is

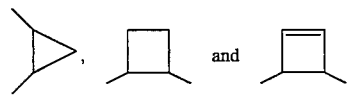

This method, which can be used to prepare compounds of this invention where X=0 and $R^2$ is specified by the dienes listed above, is illustrated with the following scheme:

Scheme D

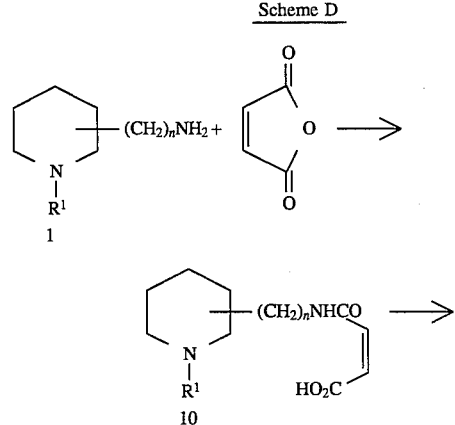

-continued
Scheme D

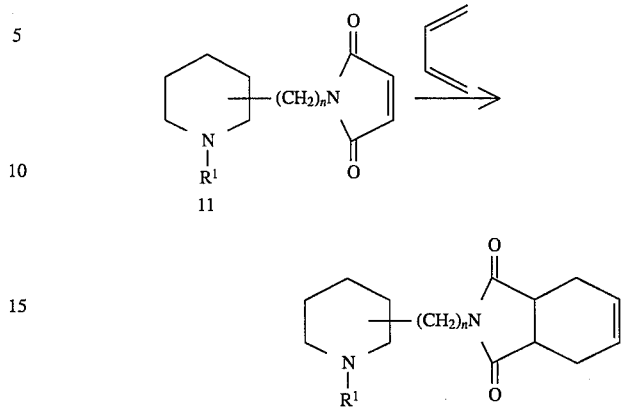

The products of the Diels-Alder reaction are optionally subjected to catalytic hydrogenation in solvents such as tetrahydrofuran, ethyl acetate, or ethanol, with catalysts such as palladium or platinium, at temperatures of about 0° to 200° C. and hydrogen pressures of 1–100 atm. to give certain compounds of this invention as illustrated by the following example:

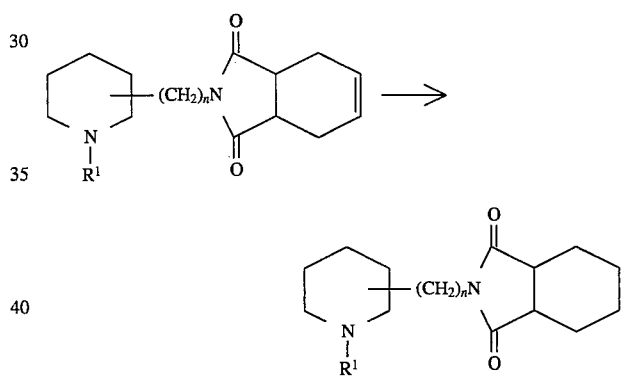

A variation of this method uses amines 3, as specified in Method B, as the starting materials. The pyridine imides of type 12 obtained in this way are converted into certain compounds of this invention by quaternization followed by reduction as described in Method B. The double bond introduced in the Diels-Alder reaction is also reduced in the last step, as illustrated in the following scheme:

Scheme D-1

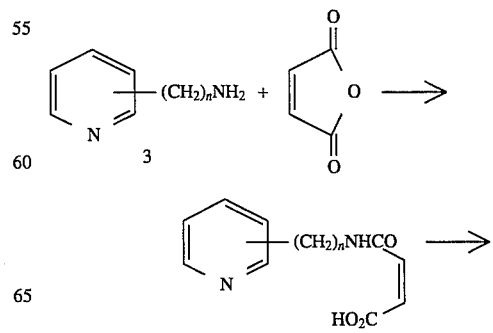

-continued
Scheme D-1

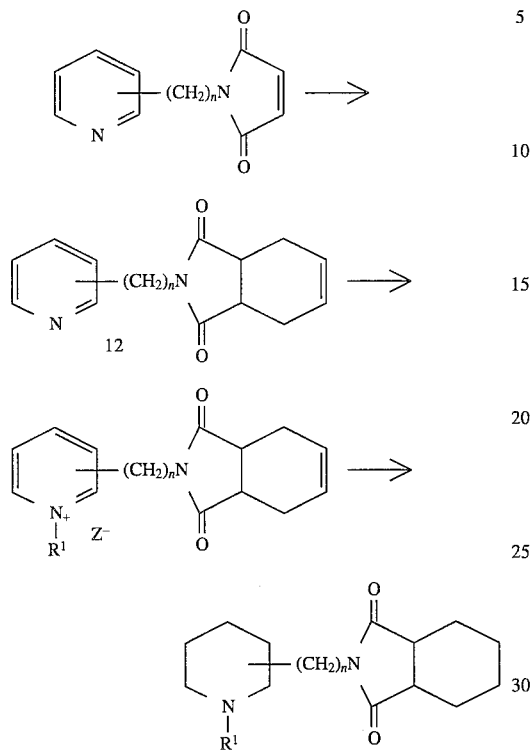

Method E

Compounds of this invention where the $(CH_2)_nR^2$ group is attached to the 2- or 4-positions of the piperidine ring, where n=2 and where X=O; $H_2$; $HR^9$; or H, $OR^9$ can be prepared as follows: compounds $R^2H$ react with 2-vinylpyridine or 4-vinylpyridine in the presence of a base such as Triton B or sodium hydride in high-boiling solvents such as N-methylpyrrolidone or, preferably, using the vinylpyridines as solvents, at temperatures of about 100°–250° C. to give imides of type 13. These are then converted into certain compounds of this invention, as specified above, by quaternization followed by reduction as described in Method B. The following scheme is an illustration of this method.

Scheme E

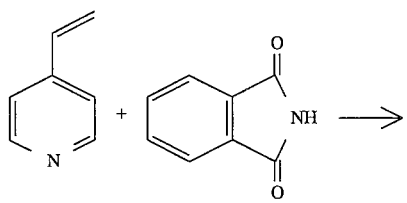

-continued
Scheme E

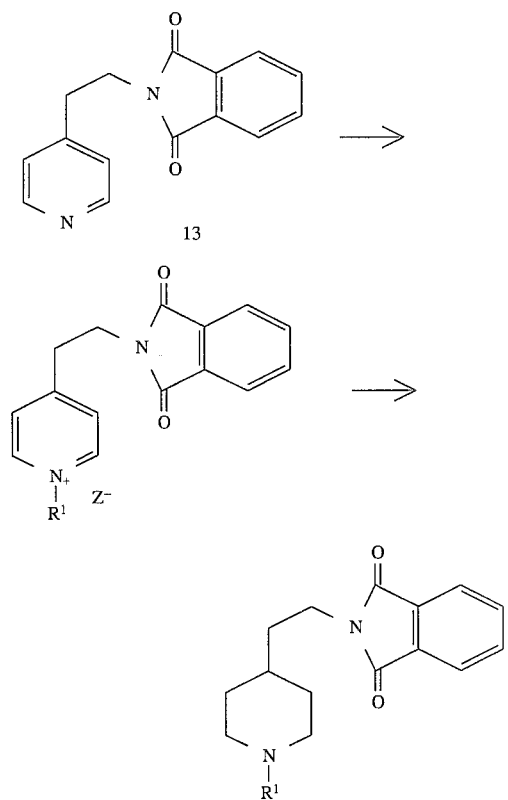

Variation of the X Substituent

Compounds of this invention where X=H, OH are made from compounds where X=O by reaction with hydride reducing agents such as sodium borohydride in methanol, or sodium borohydride in ethanol in the presence of a mineral acid such as hydrochloric acid, or lithium borohydride in an aprotic solvent such as tetrahydrofuran, at temperatures of about −20° to 60° C. as shown in the following example:

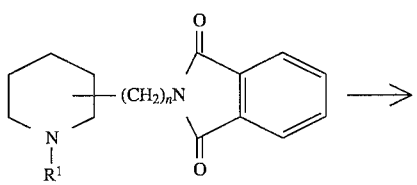

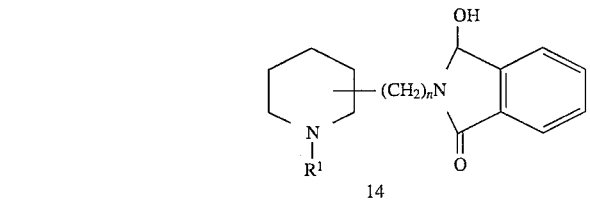

Phthalimides may also be reduced to compounds of type 14 by the action of zinc and acetic acid.

Compounds of this invention where X=H, OR⁹ are prepared from compounds where X=H, OH (such as 14 above) by reaction with an alcohol R⁹OH in the presence of an acid such as hydrochloric acid or methanesulfonic acid at temperatures of about 0°–100° C. Alternatively, compounds where X=H, OH (such as 14 above) can be treated with a base such as sodium hydride in appropriate solvents such as tetrahydrofuran, or metal alkoxides such as sodium methoxide in alcohol solvents such as methanol, followed by addition of an alkylating agent R⁹Z where Z is Cl, Br, I; OSO₂-alkyl or OSO₂-aryl, at temperatures of about 0°–100° C., for instance:

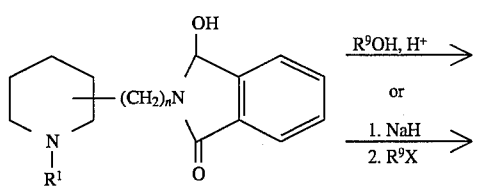

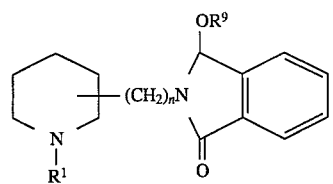

Compounds of this invention where X=R⁹, OH are made by allowing compounds where X=O to react with organometallics such as R⁹Li or R⁹MgM where M=Cl, Br, I, in aprotic solvents such as tetrahydrofuran or diethyl ether at temperatures of about −70° to +70° C. followed by hydrolysis as shown in the following example:

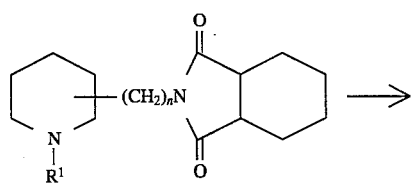

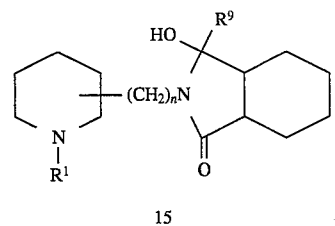

15

Compounds of this invention where X=R⁹, H are prepared from compounds where X=R⁹,OH (such as 15 above) by the action of hydride reducing agents such as sodium cyanoborohydride in the presence of a carboxylic acid such as acetic acid in solvents such as methanol at temperatures of about 0°–100° C. as illustrated in the following example:

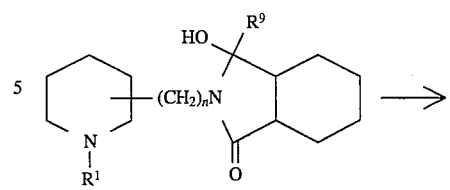

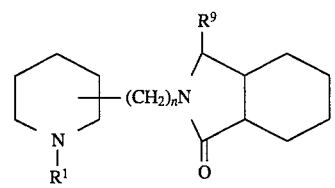

Compounds of this invention where X=R⁹, H (such as 16) are prepared from compounds where X=R⁹, OH by reaction with acids such as concentrated hydrochloric acid in ethanol at temperatures of about 0°–50° C. for instance:

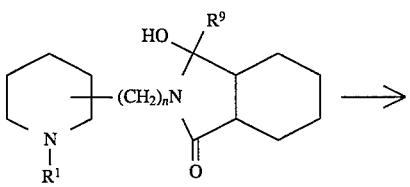

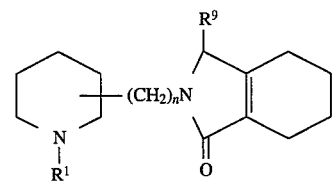

16

Compounds of this invention where X=H₂ are prepared from compounds where X=O or X=H,OH by reaction with metals such as zinc in acetic acid or tin in acetic acid in the presence of hydrochloric acid at temperatures of about 50°–200° C. for instance:

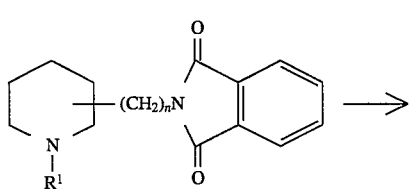

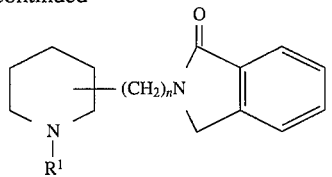

An alternate method for the preparation of compounds of this invention where X=H$_2$ uses anhydrides corresponding to R$^2$ (N- replaced by O) as starting materials. Reaction with amines 1 give the amide acids 2 as shown in Scheme A and described in Method A. Selective reduction of compounds of type 2 with diborane or with hydride reducing agents such as lithium aluminium hydride in aprotic solvents such as tetrahydrofuran at temperatures of about −30° to +30° C. give the alcohols of type 16' (below). These are converted into activated esters 17 by the action of alkyl or arylsulfonyl halides such as methanesulfonyl chloride in solvents such as tetrahydrofuran or methylene chloride in the presence of a base such as pyridine or triethylamine at temperatures of about 0° to 50° C. Treatment of compounds 17 with a base such as sodium hydride in aprotic solvents such as tetrahydrofuran or dimethylformamide gives compounds of the invention where X=H$_2$ as illustrated in the following example:

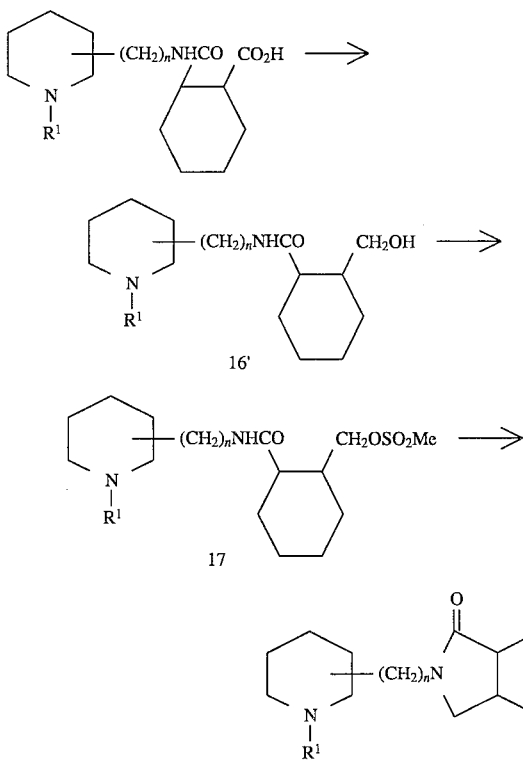

Alternatively, the anhydrides corresponding to R$^2$ (N-replaced by O) are allowed to react with alcohols such as methanol, ethanol, or t-butanol at temperatures of about 0°–100° C. to give half esters of type 18. These are reduced selectively with diborane in solvents such as tetrahydrofuran at temperatures of about −20° to 50° C. to give the alcohols of type 19. These are converted into compounds 20 where Z=Cl, Br, I, SO$_2$- alkyl or SO$_2$-aryl by well known methods, such as treatment with thionyl chloride, phosphorus tribromide or alkyl- or arylsulfonyl halides in the presence of a base such as pyridine or triethylamine. Compounds 20 are then allowed to react with amines 1 to give compounds of this invention where X=H$_2$. This method is illustrated by the following example:

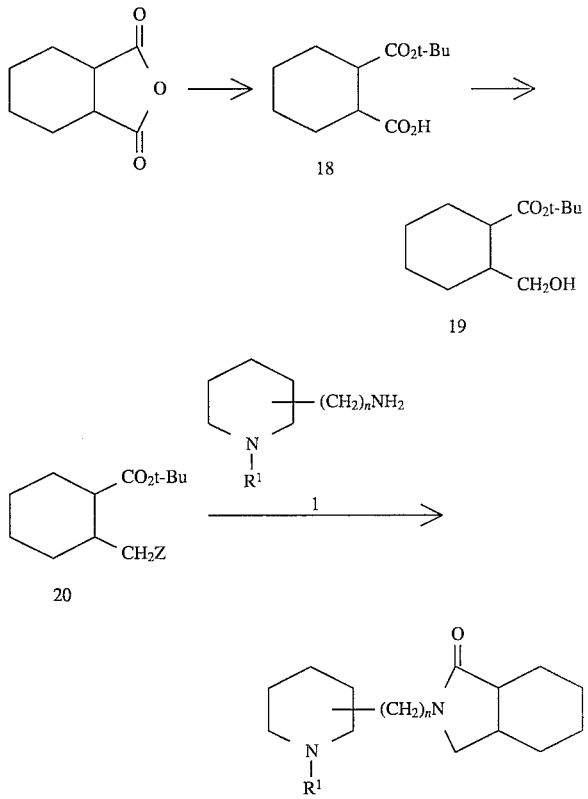

Variation of the R$^1$ Substituent

The substituent R$^1$ can be introduced as described in methods A–E above. Alternatively, a protecting group P may be used in place of R$^1$. The group P is removed at the end of the synthesis and replaced by R$^1$. For instance, a benzyl group may be used as shown in the following example. The benzyl group may be then replaced by hydrogen using well-known methods such as hydrogenolysis in the presence of a catalyst such as palladium and the R$^1$ group may be introduced by treating the secondary amine with alkylating agents R$^1$Z where Z is Cl, Br, I, OSO$_2$-alkyl or OSO$_2$-aryl in the presence of a base such as alkali carbonates at temperatures of about 0° to 150° C. in solvents such as acetonitrile or dimethylformamide.

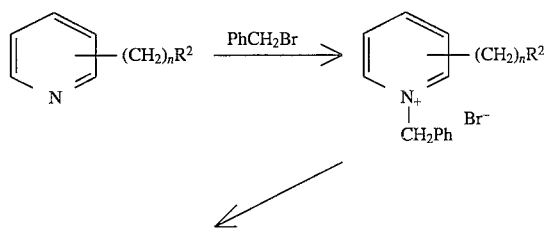

-continued

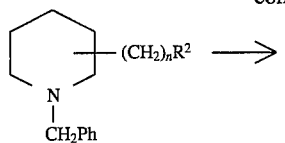

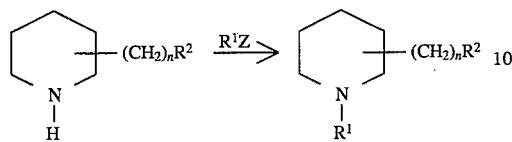

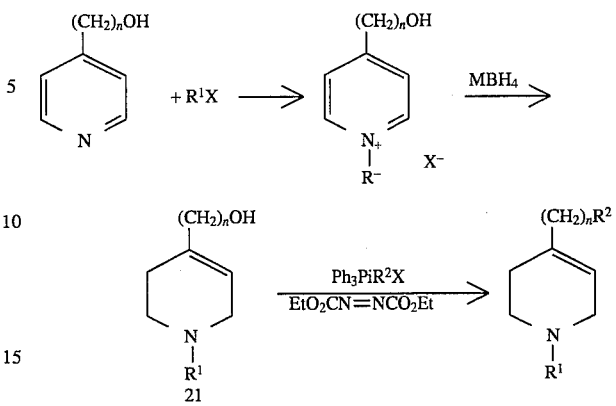

Alternatively, a methyl group may serve as a protecting group P. It may be removed by well-known methods such as reaction with cyanogen bromide followed by hydrolysis, or reaction with alkyl chloroformates followed by hydrolysis.

The invention can be further understood by the following examples in which temperatures are in degrees Centigrade and parts and percentages are by weight unless otherwise indicated.

Preparation of 3,4-Unsaturated Derivatives

Compounds where $R^2$ is attached to $C_4$ and a is a double bond are prepared by reduction of quaternary salts such as 5 with metal borohydrides such as sodium, potassium, or lithium borohydride in alcoholic solvents at low temperature (–50° to 0°):

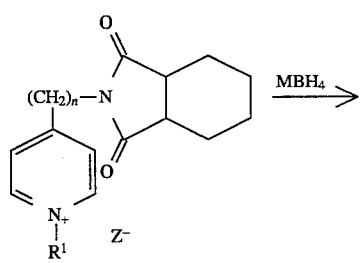

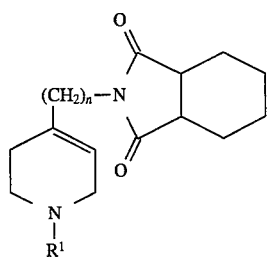

An alternate route which avoids possible complications due to reduction of the imide involves quaternization of the known 4-pyridine alkanols followed by reduction with metal borohydrides in alcohol solvents at low temperatures (–50° to 25°) to give the unsaturated alcohols 21. These are then coupled to imides $R^2H$ by reactions with triphenylphosphine and diethyl azodicarboxylate in anhydrous solvents such as tetrahydrofuren at temperatures of –20° to +60° (Mitsurobu et al., *J. Am. Chem. Soc.*, 94, 679 (1983)).

EXAMPLE 1

2-[1-(2-Phenylethyl)-4-piperidinylmethyl]-cis-3a; 4, 7, 7a-tetrahydro-1H-isoindole-1,3(2H)-dione (Method A)

($R^1$=CH$_2$CH$_2$Ph; n=1; $R^2$=

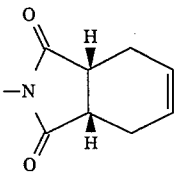

chain attached to C-4 of piperidine)

To 0.45 g (2.0 mmoles) of 1-(2-phenylethyl)-4-piperidinemethylamine was added 5 mL of dimethylformamide and 0.32 g (2.0 mmoles) of cis- 1,2,3, 6-tetrahydrophthalic anhydride. After heating 5 under reflux for 17 hours, the mixture was cooled, diluted with water, and made strongly basic with aqueous potassium hydroxide. The mixture was extracted with ethyl acetate and the extracts were washed with saturated solutions of sodium bicarbonate and sodium chloride, dried and evaporated to give 0.34 g of the title compound as a brown oil.

The fumaric acid salt had m.p. 179°–181° after crystallization from 2-propanol. NMR (CDCl$_3$:DMSO-d$_6$): δ 7.04–7.34 (m, 5H); 6.63 (s, 2H); 5.78–5.90 (s, 2H); 3.19–3.45 (d, 2H); 2.97–3.17 (m, 4H); 2.72–2.85 (m, 2H); 2.58–2.72 (m, 2H); 2.40–2.57 (m, 2H); 2.06–2.30 (m, 4H); 1.49–1.80 (m, 3H); 1.13–1.43 (m, 2H).

The starting material, 1- (2-phenylethyl) -4-piperidinemethylamine was prepared as follows:

A mixture of 1.31 g (3.8 mmoles) of 2-[1-(2-phenylethyl)-4-piperidylmethyl]-1H-isoindole-1,3(2H)-dione dione (Example 2) and 0.25 mL (7.8 mmoles) of hydrazine in 20 mL of ethanol was heated under reflux for 4 hours. The solvent was removed and the residue was made basic with aqueous potassium hydroxide and extracted with chloroform to give 0.90 g of 1-(2- phenylethyl)-4-piperidinemethylamine as an oil. NMR (CDCl₃): δ7.14–7.35 (m, 5H); 2.93–3.10 (d, 2H); 2.72–2.85 (m, 2H); 2.52–2.65(m, 4H); 1.92–2.05 (t, 2H); 1.61–1.87 (m, 2H); 1.08–1.48 (m, 5H).

EXAMPLE 2

2-[1-(2-Phenylethyl)-4-piperidinylmethyl]-1H-isoindole-1,3(2H)-dione (Method B)
(R¹=CH₂CH₂Ph; n=1; R²=

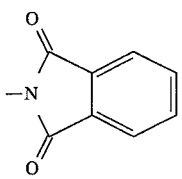

chain attached to C-4 of piperidine)

A mixture of 10.11 g of 1-(2-phenylethyl)-4-[(2,3-dihydro- 1,3-dioxo-1H-isoindol-2-yl)methyl]pyridinium bromide, 150 mL of acetic acid and 0.51 g of prereduced platinum (IV) oxide was shaken under 52 psi initial hydrogen pressure at room temperature for 6 hours. Most of the solvent was removed under reduced pressure and the residue was made strongly alkaline with 15% aqueous sodium hydroxide. Methylene chloride was added and the mixture was filtered. Separation of the layers in the filtrate, extraction of the aqueous layer with methylene chloride and removal of the solvent from the dried organic layers gave 8.04 g of the crude title compound. The hydrochloride had m.p. 277°–278° after crystallization from 90% ethanol.

Anal. Calcd. for C₂₂H₂₅ClN₂O₂: C, 68.65; H, 6.55; N, 7.28. Found: C, 68.52; H, 6.63; N, 7.33.

NMR spectrum (DMSO-d₆): δ7.9 (m, 4H); 7.2–7.4 (m, 5H); 1.5–3.6 (m, 15H).

The starting material, 1-(2-phenylethyl)-4-[(2,3-dihydro-1,3-dioxo-1H-isoindol-2-yl)methyl]pyridinium bromide, was prepared as follows:

A mixture of 74 g (0.5 mole) of phthalic anhydride, 60 g (0.56 mole) of 4-pyridinemethylamine and 200 mL of dimethylformamide was heated under reflux for 2 hours. The cooled mixture was filtered and the solids were washed with ether and dried to give 85.1 g of 2-( 4-pyridinylmethyl)-1H-isoindole-1,3(2H)-dione, m.p. 164°–165°. Another 24.0 g was obtained by crystallization of the concentrated mother liquors from dimethylformamide. Combined yield: 99.1 g (83%).

The above compound (25.1 g), 2-bromoethylbenzene (50 mL) and 100 mL of dimethylformamide were stirred at 85° bath temperature for 3 hours. The solvent was removed under vacuum, and the residue was stirred with ether. The solids were collected by filtration, washed with ether, dried, and crystallized from 95% aqueous 2-propanol to give 34.68 g of 1-(2-phenylethyl)-4-[(2,3-dihydro- 1,3-dioxo-1H-isoindol-2-yl) methyl]pyridinium bromide, m.p. 206°–208°.

NMR (DMSO-d₆): 9.0 (d, 2H); 8.2 (d, 2H); 7.8–8.0 (m, 4H); 7.2–7.4 (m, 5H); 5.0 (s, 2H); 4.8 (t, 2H) and 3.2 (t, 2H).

EXAMPLE 3

2-[1-(2-Phenylethyl)-4-piperidinylmethyl]-cis-3a,4,5,6,7,7a-hexahydro-1H-isoindole-1,3(2H)-dione
(Method B)

(R¹=CH₂CH₂Ph; n=1; R²=

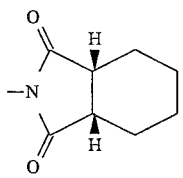

chain attached to C-4 of piperidine)

To 10.0 g (23 mmoles) of 4-[(cis-octahydro-1,3-dioxo-1H-isoindol-2-yl)methyl]-1-(2-phenylethyl) pyridinium bromide was added 200 mL of glacial acetic acid and 1.0 g of platinum (IV) oxide. The mixture was hydrogenated at 50 p.s.i. and room temperature for 2.5 hours. The reaction mixture was filtered, concentrated, and the residue was dissolved in water. The aqueous solution was made strongly basic with aqueous sodium hydroxide, and extracted with ethyl acetate. The organic extracts were washed with saturated sodium bicarbonate solution and saturated sodium chloride solution, dried and evaporated to afford 7.61 g (92% yield) of the title compound. The fumaric acid salt was crystallized from 2-propanol and had m.p. 199°–200°; NMR (DMSO-d₆): δ7.17–7.48 (m, 5H); 6.6 (s, 2H); 3.23–3.34 (d, 2H); 3.07–3.22 (d, 2H); 2.90–3.00 (m, 2H); 2.69–2.86 (m, 4H); 2.21–2.40 (t, 2H); 1.48–1.89 (m, 7H); 1.14–1.48 (m, 6H).

Anal. Calcd. for C₂₆H₃₄N₂O₆: C, 66.36; H, 7.28; N, 5.95. Found: C, 66.35; H, 7.41; N, 5.94.

The starting material, 4-[(cis-octahydro-1,3-dioxo-1H-isoindol-2-yl)methyl]-1-(2-phenylethyl) pyridinium bromide was prepared as follows.

To 17.0 g (157 mmoles) of 4-aminomethylpyridine was added 40 mL of dimethylformamide and 24.2 g (157 mmoles) of cis-1,2-cyclohexanedicarboxylic anhydride. The mixture was heated under reflux for 2 hours. The cooled solution was diluted with water, made basic with aqueous potassium hydroxide, and extracted with ethyl acetate. The organic extracts were washed with saturated sodium bicarbonate solution and saturated sodium chloride solution, dried and evaporated to afford 16.8 g of 2-(4-pyridinylmethyl)-cis- 3a,4,5,6,7,7a-hexahydro-1H-isoindole- 1,3(2H)-dione, m.p. 91°–92°; NMR (CDCl₃): δ 8.53–8.63 (d, 2H); 7.19–7.29 (d, 2H); 4.63 (s, 2H); 2.80–3.00 (m, 2H); 1.78–2.00 (m, 2H); 1.63–1.78 (m, 2H); 1.33–1.58 (m, 4H).

To 16.8 g (68 mmoles) of the above compound was added 70 mL of 2-propanol and 12.6 g (68 mmoles) of 2-bromoethylbenzene. The mixture was heated under reflux for 24 hours, and then cooled in an ice bath. The precipitated solid was collected by suction filtration and washed with cold ethyl ether to afford 19.85 g (67% yield) of 4-[(cis-octahydro-1,3-dioxo-1H-isoindol-2-yl) methyl]-1(2-phenylethyl) pyridinium bromide, m.p. 208° ; NMR (DMSO-d₆): δ9.03–9.10 (d, 2H); 7.96–8.07 (d, 2H); 7.20–7.37 (m, 5H); 4.82–4.97 (m, 4H); 3.22–3.36 (t, 2H); 3.08–3.20 (m, 2H);

1.72–1.90 (m, 2H); 1.54–1.72 (m, 2H); 1.26–1.54 (m, 4H) .
cl ,EXAMPLE 4

2-[3-[1-(phenylmethyl)-3-piperidinyl]propyl]-
1H-isoindole- 1,3(2H)-dione (R¹=CH₂Ph; n=3; R²=

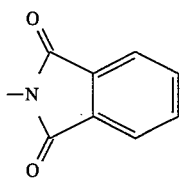

chain attached to C-3 of piperidine)

A mixture of 1.10 g (2.5 mmol) of 3-[3-(2,3-dihydro-1,3-dioxo-1H-isoindol-2-yl)propyl]-1-(phenylmethyl)pyridinium bromide, 50 mL of glacial acetic acid and 0.11 g of platinum oxide was hydrogenated at room temperature and atmospheric pressure for 6 hours with rapid stirring. The reaction mixture was filtered and concentrated, and the residue was dissolved in water. The aqueous solution was made strongly basic with aqueous potassium hydroxide and extracted several times with ethyl acetate. The combined organic extracts were washed with a saturated sodium bicarbonate solution and a saturated sodium chloride solution, dried and evaporated to give 0.77 g of 2-[3-[1-(phenylmethyl)-3-piperidinyl]propyl]-1H-isoindole- 1,3(2H)-dione as a yellow oil.

The fumaric acid salt had m.p. 151°–152° after crystallization from 2-propanol.

Anal. Calcd. for $C_{23}H_{30}N_2O_6$: C, 67.77; H, 6.32; N, 5.85. Found: C, 67.50; H, 6.29 N, 6.01.

The starting material, 3-[3-(2,3-dihydro-1,3-dioxo- 1-H-isoindol-2-yl)propyl]-1-(phenylmethyl)pyridinium bromide, was prepared as follows:

To 17.0 g (124 moles) of 3-(3-pyridyl)-1-propanol was added 240 mL of 48% hydrobromic acid. The mixture was heated under reflux for 4 hours, and then evaporated to dryness to afford the hydrobromide salt of 3-(3-pyridyl)-1-bromopropane as an oil in quantitative yield.

NMR (CDCl₃): δ16.40–16.94 (bs, 1H); 8.76–9.00 (m, 2H); 8.29–8.46 (d, 1H); 7.96–8.18 (m, 1H); 3.32–3.53 (t, 2H); 3.00–3.19 (t, 2H); 2.16–2.41 (m, 2H).

To 7.9 g (28 mmoles) of 3-(3-pyridyl)-1-bromopropane HBr was added 150 mL of dimethylformamide and 27.0 g (145 moles) of potassium phthalimide. The reaction mixture was heated under reflux for 3 hours. The mixture was cooled, diluted with water, and made basic with aqueous potassium hydroxide. The product was then extracted with ethyl acetate, and the extracts were washed with saturated solutions of sodium bicarbonate and sodium chloride, dried and evaporated to give 11.0 g of 2-[3-(3-pyridinyl)propyl]-1H-isoindole-1,3(2H)-dione, m.p. 88°–90°; NMR (CDCl₃) δ8.36–8.50 (m, 2H); 7.75–7.90 (m, 2H); 7.57–7.75 (m, 2H); 7.47–7.56 (d, 1H); 7.13–7.32 (m, 1H); 3.63–3.29 (t, 2H); 2.53–2.71 (t, 2H); 1.94–2.10 (m, 2H) .

A mixture of 2.00 g (7.5 moles) of 2-[3-(3-pyridinyl) propyl]-1H-isoindole-1,3 (2H) -dione, 8 mL of 2-propanol, and 1.71 g (10 mmoles) of benzyl bromide was heated under reflux for 1 hour. The solution was cooled to 0°, and the precipitated product was collected by suction filtration, washed with cold ethyl ether, and dried to afford 3.08 g of 3-[3-(2,3-dihydro-1,3-dioxo- 1H-isoindol-2-yl)propyl]-1-(phenylmethyl)pyridinium bromide.

NMR (CDCl₃/DMSO-d₆) δ59.45–9.56 (d, 1H); 9.39–9.44 (s, 1H); 8.18–8.29 (d, 1H); 7.90–8.00 (t, 1H); 7.12–7.91 (m, 6H); 7.29–7.46 (m, 3H); 6.28 (s, 2H); 3.58–3.77 (t, 2H); 2.78–2.97 (t, 2H); 2.04–2.23 (m, 2H).

EXAMPLE 5 cis-Octahydro-3-hydroxy-2-[[1-(2-phenylethyl)-
4-piperidinyl]methyl]- 1H-isoindol-1-one (R¹=CH₂CH₂Ph; n=1; R²=

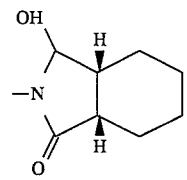

chain attached to C-4 of piperidine)

To 2.25 g (6.3 mmoles) of 2-[1-(2-phenylethyl)-4-piperidinylmethyl]-cis- 3a,4,5,6,7,7a-hexahydro-1H-isoindole-1,3(2H)-dione (Example 3) dissolved in 10 mL of methanol was added 0.42 g (11 moles) of sodium borohydride in portions with stirring at 0°. The mixture was stirred at 0° for 2.5 hours. To the reaction mixture was added 15 mL of precooled water and the product was extracted with chloroform. The dried organic phase was evaporated to afford 1.90 g of the title compound.

The fumaric acid salt had m.p. 211°–213° C. after crystallization from 2-propanol.

Anal. Calcd. for $C_{26}H_{36}N_2O_6$: C, 66.08; H, 7.68; N, 5.93. Found: C, 66.13; H, 7.72; N, 5.81

NMR (DMSO-d₆) δ7.13–7.22 (m, 5H): 6.63 (s, 2H); 5.04–5.10 (d, 1H); 2.98–3.33 (m, 4H); 2.83–2.93 (m, 4H); 2.37–2.58 (m, 2H); 2.29–2.37 (m, 2H); 1.12–1.93 (m, 13H).

EXAMPLE 6

2,3,4,5,6,7-hexahydro-2-[[1-(2-phenylethyl)-
4-piperidinyl] methyl]-1H-isoindol-1-one (R¹=CH₂CH₂Ph; n=1; R²=

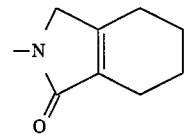

chain attached to C-4 of piperidine)

Concentrated hydrochloric acid was added dropwise to 0.85 g (2.4 mmoles) of cis-octahydro-3-hydroxy-2-[[1-( 2-phenylethyl)-4-piperidinyl]methyl]-1H-isoindol-1-one (Example 5) dissolved in 20 mL of ethanol until the solution maintained a pH of 3–4. The mixture was stirred at 0° for 40 minutes, and was then evaporated to dryness. The residual oil was dissolved in water, and the mixture was made strongly basic with aqueous sodium hydroxide. The aqueous phase was extracted with chloroform and the extracts were dried and evaporated to give 0.75 g of the title compound as a clear oil.

NMR (CDCl₃): 7.13–7.36 (m, 5H); 3.75–3.80 (s, 2H); 3.26–3.35 (d, 2H); 2.91–3.06 (m, 2H); 2.75–2.86 (m, 2H); 2.51–2.60 (m, 2H); 2.15–2.30 (m, 4H); 1.92–2.07 (t, 2H); 1.50–1.81 (m, 7H); 1.29–1.47 (m, 2H).

The salt with fumaric acid had m.p. 211°–212° after crystallization from 2-propanol. Anal. Calcd. for $C_{26}N_2O_5H_{34}\cdot 0.5H_2O$: C, 67.36; H, 7.61; N, 6.04. Found: C, 67.74; H, 7.47; N, 6.05.

$^{13}$C NMR (DMSO-$d_6$): δ19.9; 21.4; 21.6; 23.4; 27.7; 30.9; 33.7; 46.3; 53.3; 57.7; 51.4; 126.1; 128.2; 128.5; 130.1; 134.5; 138.7; 150.4; 167.1; 170.9.

EXAMPLE 7

2,3-Dihydro-3-hydroxy-2-[[1-(2-phenylethyl)-4-piperidinyl] methyl]-1H-isoindol-1-one ($R^1=CH_2CH_2Ph$; n=1; $R^2=$

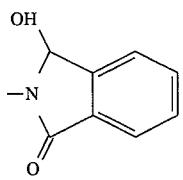

chain attached to C-4 of piperidine)

To a mixture of 2.0 g (5.7 mmoles) of 2-[1-(2-phenylethyl)- 4-piperidinylmethyl]-1H-isoindole-1,3(2H)-dione (Example 2) and 2.04 g (31 mmoles) of zinc dust in 30 mL of glacial acetic acid was stirred at room temperature for 45 minutes. The excess solvent was removed from the filtered mixture by evaporation, and aqueous sodium bicarbonate was added to the residue. The aqueous mixture was extracted with ethyl acetate and the extracts were washed with saturated sodium chloride, dried and evaporated to afford 0.85 g of the title compound as a foam.

NMR (CDCl$_3$): δ7.41–7.75 (m, 4H); 7.14–7.35 (m, 5H); 5.83 (s, 1H); 3.40–3.52 (m, 1H); 3.15–3.27 (m, 1H); 2.68–2.90 (m, 4H); 2.43–2.58 (m, 2H); 1.72–2.01 (m, 3H); 1.52–1.72 (m, 2H); 1.01–1.30 (m, 2H).

The fumaric acid salt had m.p. 219°–221° after crystallization from 2-propanol.

EXAMPLE 8 cis-Octahydro-3-hydroxy-3-methyl-2-[[1-(2-phenylethyl)4-piperidinyl] methyl]-1H-isoindol-1-one ($R^1=CH_2CH_2Ph$; n=1; $R^2=$

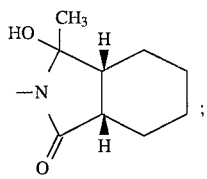

$R^2$ attached to C-4 of piperidine)

To 0.90g (2.5 mmol) of 2-[1-(2-phenylethyl)-4-piperidinylmethyl]-cis- 3a, 4, 5, 6, 7, 7a-hexahydro-1H-isoindole-1,3(2H)-dione under nitrogen was added 10 ml dry THF. The mixture was cooled to 0° and 2.0 ml (2.8 mmol) of 1.4 M methyllithium in ether was slowly added to the stirring solution. Stirred at 0° continued for 35 minutes. The reaction mixture was quenched by the slow addition of saturated ammonium chloride solution, and the product extracted with methylene chloride. The organic extracts were dried over MgSO$_4$ and evaporated to afford 0.72 g of the title compound as a clear oil which solidified upon standing. The fumaric acid salt had m.p. 140–142 after crystallization from 2-propanol.

Anal. Calcd. for $C_{27}H_{38}N_2O_6$:C,66.64; H, 7.87; N, 5.76. Found C, 66.47; H, 7.92, N, 5.54. NMR (DMSO-d6) 7.15–7.32 (m, 5H); 6.56 (s, 2H); 3.01–3.18 (m, 3H); 2.69–2.91 (m, 5H); 2.38–2.47 (m, 1H); 2.16–2.33 (m, 2H); 1.97–2.11 (m, 1H); 1.72–1.92 (m, 2H); 1.53–1.71 (m, 4H); 1.00–1.50 (m, 10H).

In the following tables, N denotes the carbon atom of the piperidine ring to which the $(CH_2)_nR^2$ group is attached.

TABLE 1

| Ex. | N | n | $R^1$ | $R^2$ | m.p. (°C.) |
|---|---|---|---|---|---|
| 1 | 4 | 1 | $(CH_2)_2Ph$ | (cyclohexene diimide structure) | 179–181[a] |
| 2 | 4 | 1 | $(CH_2)_2Ph$ | (phthalimide structure) | 277–278[b] |

TABLE 1-continued (structure: 4-substituted piperidine with (CH₂)ₙR² at 4-position and R¹ on N)

| Ex. | N | n | R¹ | R² | m.p. (°C.) |
|---|---|---|---|---|---|
| 3 | 4 | 1 | (CH₂)₂Ph | cis-hexahydrophthalimide | 199–200[a] |
| 4 | 3 | 3 | CH₂Ph | phthalimide | 151–152[a] |
| 5 | 4 | 1 | (CH₂)₂Ph | 3-hydroxymethyl-hexahydroisoindolin-1-one | 211–213[a] |
| 6 | 4 | 1 | (CH₂)₂Ph | 4,5,6,7-tetrahydroisoindol-1(2H)-one | 211–212[a] |
| 7 | 4 | 1 | (CH₂)₂Ph | 3-hydroxy-2,3-dihydroisoindol-1-one | 219–221[a] |
| 8 | 4 | 1 | (CH₂)₂Ph | 3-(1-hydroxy-1-methylethyl)-hexahydroisoindolin-1-one | 140–142[a] |
| 9 | 4 | 2 | —(CH₂)₂Ph | 1H-benz[de]isoquinoline-1,3(2H)-dione | 147 (dec) |

TABLE 1-continued

| Ex. | N | n | R¹ | R² | m.p. (°C.) |
|---|---|---|---|---|---|
| 10 | 4 | 1 | —(CH$_2$)$_2$-3-indolyl | (tricyclic imide) | 212 (dec)[a] |
| 11 | 4 | 1 | (CH$_2$)$_2$Ph | (naphthalimide) | 228 (dec)[b] |

Footnotes for Table 1
[a] Fumarate salt.
[b] Hydrochloride salt.

TABLE 2

| Ex. | N | n | R¹ | R⁵ | Ring Junction Stereochemistry | m.p. (°C.) |
|---|---|---|---|---|---|---|
| 12 | 4 | 0 | CH$_2$Ph | H | cis | 198–199 |
| 13 | 4 | 0 | (CH$_2$)$_2$Ph | H | cis | 217 |
| 14 | 4 | 1 | CH$_2$Ph | H | cis | 181–183 |
| 15 | 4 | 1 | CH$_2$C$_6$H$_{11}$ | H | cis | 217–219 |
| 16 | 4 | 1 | (CH$_2$)$_3$Ph | H | cis | 196–197 |
| 17 | 4 | 1 | (CH$_2$)$_2$C$_6$H$_{11}$ | H | cis | 217–218 |
| 18 | 4 | 1 | CH$_2$C$_6$H$_4$CF$_3$-3 | H | cis | 179–180 |
| 19 | 4 | 1 | (CH$_2$)$_2$C$_6$H$_4$OH-4 | H | cis | 215–217 |
| 20 | 4 | 1 | CH$_2$C$_6$H$_4$F-4 | H | cis | 179–180 |
| 21 | 4 | 1 | CH$_2$-cyclopropyl | H | cis | 159–161 |
| 22 | 4 | 1 | CH$_2$CH$_2$Ph | H | trans | 192–193 |
| 23 | 4 | 1 | CH$_2$CH$_2$Ph | Me | cis | 170–171 |
| 24 | 4 | 2 | CH$_2$CH$_2$Ph | H | cis | 207–208 |
| 25 | 4 | 1 | —(CH$_2$)$_2$C$_6$H$_4$OH-4 | H | cis | 215–217 |
| 26 | 4 | 1 | —(CH$_2$)$_2$C$_6$H$_4$Cl-4 | H | cis | 185–188 |
| 27 | 4 | 1 | —(CH$_2$)$_2$C$_6$H$_4$NO$_2$-4 | H | cis | 169–171 |
| 28 | 4 | 1 | —(CH$_2$)$_2$C$_6$H$_4$N(CH$_3$)$_2$-4 | H | cis | 203 (dec.) |
| 29 | 4 | 1 | —(CH$_2$)$_2$C$_6$H$_4$F-4 | H | cis | 174 (dec.) |
| 30 | 4 | 1 | (CH$_2$)$_2$C$_6$H$_4$Br-4 | H | cis | 196 |
| 31 | 4 | 1 | (CH$_2$)$_2$C$_6$H$_4$CF$_3$-4 | H | cis | 186–188 |
| 32 | 4 | 1 | (CH$_2$)$_2$-3-indolyl | H | cis | 188 (dec.) |
| 33 | 4 | 3 | (CH$_2$)$_2$Ph | H | cis | 167–168 |

TABLE 3

![Structure: piperidine-N-R¹ with (CH₂)ₙ linker to phthalimide; fumaric acid salt]

| Ex. # | N | n | R¹ | m.p. (°C.) |
|---|---|---|---|---|
| 34 | 4 | 1 | $CH_2C_6H_5$ | >220 |
| 35 | 4 | 1 | $CH_2C_6H_4F-3$ | >220 |
| 36 | 4 | 1 | $CH_2C_6H_4F-4$ | >220 |
| 37 | 4 | 1 | $CH_2$-cyclopropyl | 194–196 |
| 38 | 4 | 2 | $CH_2C_6H_5$ | 163–165 |
| 39 | 4 | 2 | $(CH_2)_2C_6H_5$ | 183–185 |
| 40 | 4 | 2 | $CH_2C_6H_4F-3$ | 179–181 |
| 41 | 4 | 2 | $CH_2C_6H_4F-4$ | 177–178 |
| 42 | 4 | 2 | $CH_2$-cyclopropyl | 119–121 |
| 43 | 4 | 3 | $CH_2C_6H_5$ | 180–182 |
| 44 | 4 | 3 | $(CH_2)_2C_6H_5$ | 161–162 |
| 45 | 3 | 0 | $CH_2C_6H_5$ | 188–191 |
| 46 | 3 | 0 | $(CH_2)_2C_6H_5$ | 171 (dec.) |
| 47 | 3 | 1 | $CH_2C_6H_5$ | 214–216 |
| 48 | 3 | 1 | $(CH_2)_2C_6H_5$ | 195 (dec.) |
| 49 | 3 | 3 | $(CH_2)_2C_6H_5$ | 127–130 |
| 50 | 2 | 2 | $CH_2C_6H_5$ | 103 (dec) |
| 51 | 2 | 2 | $(CH_2)_2C_6H_5$ | 65 (dec) |

TABLE 4

![Structure: 4-(CH₂R²)-1-phenethylpiperidine; fumaric acid salt]

| Example # | R² | m.p. (°C.) |
|---|---|---|
| 52[a] | ![cyclohexene-fused succinimide] | 220–223 |
| 53 | ![norbornane-fused succinimide] | 204–206 |
| 54 | ![norbornane-fused succinimide with CH₂] | 227–228 |
| 55 | ![norbornene-fused succinimide] | 199–200 |
| 56 | ![tetrahydrophthalimide] | 207–210 |
| 57[b] | ![benzo-fused bicyclic imide] | 198–200 (dec) |
| 58[c] | ![oxa-bridged bicyclic imide] | >220 |
| 59[c] | ![cyclobutene-fused norbornene imide] | >230 |
| 60 | ![cyclobutene-fused norbornene imide] | 197 (dec) |
| 61[c] | ![bicyclic imide] | >230 |

TABLE 4-continued

R² structures with piperidine-phenethyl-fumarate scaffold

| Example # | R² | m.p. (°C.) |
|---|---|---|
| 62 | bicyclic imide with bridged alkene | 187 (dec) |
| 63[b] | dihydroxy cyclohexane-fused imide | 218 (dec) |
| 64 | methyl-substituted hexahydroisoindoledione (CH₃, H) | 181–184 |
| 65 | dimethyl-substituted hexahydroisoindoledione (CH₃, CH₃) | 179–182 |
| 66 | dimethyl tetrahydroisoindoledione with alkene (CH₃, CH₃) | 190–192 |
| 67 | methyl tetrahydroisoindoledione with alkene (CH₃, H) | 172 (dec) |
| 68 | diphenyl-substituted hexahydroisoindoledione (Ph, Ph) | 201 (dec) |
| 69 | norbornene-fused imide | 187–188 |
| 70 | methyl-substituted tetrahydroisoindolone | 250 (dec) |
| 71 | bridged bicyclic isoindolone | 191 (dec) |
| 72 | tricyclic imide with cyclobutane | 203 |
| 73 | bridged bicyclic hydroxy isoindolone (HO, H) | 138 (dec) |

[a] hydrochloride
[b] ratio of base:fumaric acid = 2:1
[c] hydrobromide

TABLE 4a

Structure: 1-(2-phenylethyl)-4-hydroxy-4-((CH$_2$)$_n$R$^2$)piperidine · fumaric acid (HO$_2$C-CH=CH-CO$_2$H)

| Ex. # | R$^2$ | (m.p. °C.) |
|---|---|---|
| 74 | cis-hexahydrophthalimido (N-yl) | 218 (dec) |
| 75 | bicyclic alkene dicarboximido | 224–226 |
| 76 | tricyclic alkene dicarboximido | >230 |
| 77 | tricyclic cyclobutane-fused dicarboximido | >230 |

TABLE 5

Structure: 1-R$^1$-4-((CH$_2$)$_n$R$^2$)piperidine

| Ex. # | R$^1$ | R$^2$ | X | n | N |
|---|---|---|---|---|---|
| 78 | CH$_2$-cyclopropyl | 5-chloro-2-(N-methyl-carboxamido)benzyl-imino (dihydroisoquinolinone-type) | CH$_3$, H | 0 | 2 |
| 79 | (CH$_2$)$_2$-cyclopentyl | 6-nitro-naphthalene-2,3-dicarboximido | 4-CH$_3$C$_6$H$_4$, OH | 1 | 3 |
| 80 | (CH$_2$)$_4$-cyclohexyl-C$_2$H$_5$ | 5-methyl-naphthalene-2,3-dicarboximido | O | 2 | 4 |
| 81 | CH$_2$-cyclooctyl | 7-methyl-6-(benzoylamino)-dihydronaphthalene-2,3-dicarboximido | H, OCH$_3$ | 2 | 4 |

TABLE 5-continued

[Structure: piperidine with N-R¹ substituent and 4-position bearing (CH₂)ₙR² group]

| Ex. # | R¹ | R² | X | n | N |
|---|---|---|---|---|---|
| 82 | CH₂C₆H₄Cl-m | [decahydronaphthalene-fused succinimide] | H, OH | 3 | 4 |
| 83 | (CH₂)₂C₆HCF₃-p | [naphthalene-fused imide] | O | 2 | 4 |
| 84 | (CH₂)₃C₆H₄NO₂-o | [tetrahydronaphthalene-fused imide] | H₂ | 4 | 4 |
| 85 | (CH₂)₄C₆H₄SOCH₃-m | [CN-substituted dihydronaphthalene-fused N-methyl imide] | O | 2 | 4 |
| 86 | (CH₂)₂C₆H₅ | [dihydronaphthalene-fused N-methyl imide] | H, n-C₃H₇ | 2 | 4 |
| 87 | (CH₂)₂C₆H₅ | [NH₂-substituted dihydronaphthalene-fused N-methyl imide] | O | 1 | 4 |
| 88 | (CH₂)₂C₆H₅ | [decahydronaphthalene-fused imide] | H, OH | 2 | 4 |

TABLE 5-continued
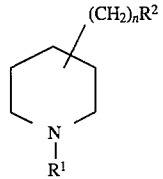
| Ex. # | R¹ | R² | X | n | N |
|---|---|---|---|---|---|
| 89 | $(CH_2)_2C_6H_5$ | 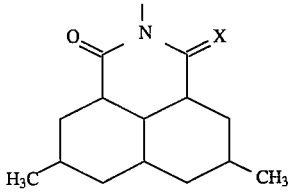 | $H_2$ | 1 | 4 |
| 11 | $(CH_2)_2C_6H_5$ | 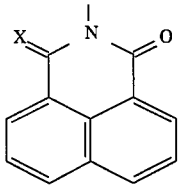 | O | 1 | 4 |
| 90 | $(CH_2)_2C_6H_5$ | 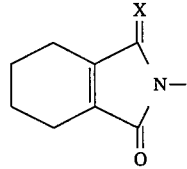 | H, $OC_2H_5$ | 2 | 4 |
| 91 | $(CH_2)_2C_6H_5$ | 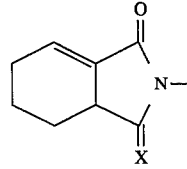 | H, OH | 3 | 3 |
| 92 | $(CH_2)_3C_6H_4NH_2$-m | 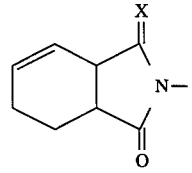 | O | 4 | 4 |
| 93 | $(CH_2)_2C_6H_4NHCOC_2H_5$-m | 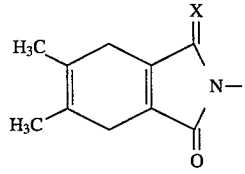 | $H_2$ | 2 | 4 |
| 94 | $(CH_2)_3C_6H_5$ | 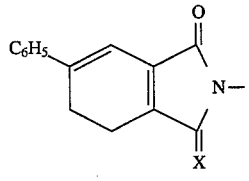 | O | 1 | 4 |

TABLE 5-continued

Structure: piperidine with N-R¹ and 4-(CH₂)ₙR²

| Ex. # | R¹ | R² | X | n | N |
|---|---|---|---|---|---|
| 95 | (CH₂)₂C₆H₅ | tetrahydroisoindole-1,3-dione (with double bond) | H₂ | 2 | 3 |
| 96 | (CH₂)₂C₆H₄Br-m | 5-chloro-hexahydroisoindole-1,3-dione | C₆H₅, OH | 1 | 4 |
| 97 | (CH₂)₂C₆H₄C₆H₅-m | 7a-methyl-hexahydroisoindole-1,3-dione | H, OH | 1 | 4 |
| 98 | (CH₂)₂-cyclopentyl | 4-phenyl-hexahydroisoindole-1,3-dione | H, OC₂H₅ | 1 | 4 |
| 99 | (CH₂)₂Ph | 5-hydroxy-hexahydro-cyclopenta[c]pyrrole-1,3-dione | H₂ | 2 | 4 |
| 100 | (CH₂)₂C₆H₄OMe-m | tetrahydroisoindole (with double bond) | H, CH₃ | 1 | 4 |
| 101 | (CH₂)₂C₆H₅ | hexahydroisoquinoline-1,3-dione | O | 1 | 4 |
| 102 | (CH₂)₂C₆H₅ | hexahydroisoquinoline-1,3-dione | H, OH | 1 | 4 |

TABLE 5-continued
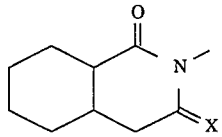
| Ex. # | R¹ | R² | X | n | N |
|---|---|---|---|---|---|
| 103 | (CH₂)₂C₆H₅ | 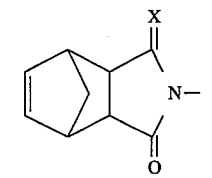 | H₂ | 1 | 4 |
| 104 | (CH₂)₂C₆H₄OH-m | 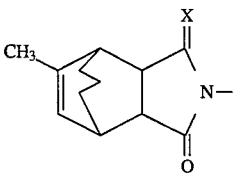 | H, OH | 1 | 4 |
| 105 | (CH₂)₂C₆H₅ | 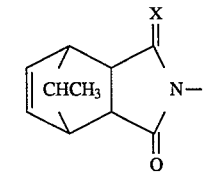 | H, OCH₃ | 1 | 4 |
| 106 | (CH₂)₂C₆H₅ | 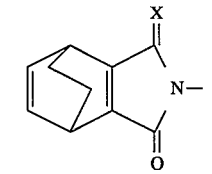 | H₂ | 2 | 4 |
| 107 | CH₂C₆H₅ | 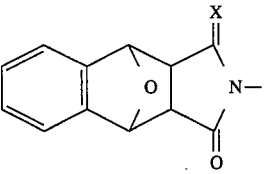 | O | 1 | 4 |
| 108 | (CH₂)₂C₆H₅ | 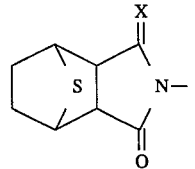 | O | 1 | 4 |
| 109 | (CH₂)₂C₆H₅ |  | H, OH | 1 | 4 |
| 110 | (CH₂)₂C₆H₅ |  | O | 1 | 4 |

TABLE 5-continued

| Ex. # | R¹ | R² | X | n | N |
|---|---|---|---|---|---|
| 111 | $(CH_2)_2C_6H_5$ | (norbornane-fused imide) | $H_2$ | 2 | 4 |
| 112 | $(CH_2)_3C_6H_5$ | (bicyclic alkene-fused imide) | O | 1 | 4 |
| 113 | $(CH_2)_2C_6H_5$ | (bicyclic diene-fused imide) | O | 1 | 4 |

EXAMPLE 70

2, 3, 4, 5, 6, 7,
-hexahydro-2-[[1-(2-phenylethyl)-4-piperidinyl]methyl]-
3-methyl-1H-isoindol-1-one ($R^1=CH_2CH_2Ph$; n=1; $R^2$ attached to C-4 of piperidine)
$R^2$ =

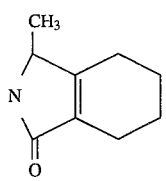

To 2.30 g (6.2 mmol) of cis-octahydro-3-hydroxy-3-methyl- 2-[[1-(2-phenylethyl)4-piperidinyl]methyl]-1H-isoindol- 1-one was added 60 mL of ethanol. The mixture was cooled to 5° C., and c. HCl (1–2 mL) was added dropwise until a pH of <2 was maintained by the stirring solution. Excess ethanol was removed by evaporation, and the residue dissolved in water. The aqueous phase was basified with potassium carbonate to pH>9, and the product extracted with ethyl acetate. The extracts were dried and evaporated to give the title compound as a yellow oil in quantitative yield.

NMR (CDCl$_3$): δ7.15–7.31 (m, 5H); 3.81–3.89 (m, 1H); 3.60–3.69 (m, 1H); 2.87–3.06 (m, 3H); 2.73–2.84 (m, 2H); 2.49–2.60 (m, 2H); 2.06–2.31 (m, 3H); 1.91–2.03 (m, 2H); 1.55–1.62 (m, 8H); 1.26–1.44 (m, 2H); 1.16–1.21 (d, 3H).

The hydrochloride salt had m.p. 250 ° C. after crystallization from ethanol/ether. Anal. Calcd. for $C_{23}H_{33}N_2OCl$: C, 71.02; H, 8.55; N, 7.20; Cl, 9.11. Found: C, 70.86; H, 8.63; N, 7.13; Cl, 9.16.

EXAMPLE 114

2-[1-(2-Phenylethyl)-4-(1, 2, 3,
6-tetrahydropyridinyl)
methyl]-1H-isoindole-1,3(2H)-dione.

($R^1=CH_2CH_2Ph$; n=1, $R^2$=

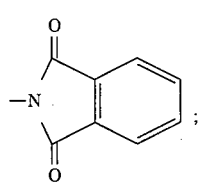

a=double bond; $R^2$ is attached to C-4 of piperidine)

To a mixture of 2.2g of 1-(2-phenylethyl)-1,2,3,6-tetrahydro- 4-pyridinemethonol, 1.5 g of phthalimide, 2.6 g of triphenylphosphine and 15 mL of dry tetrahydrofuran was added, over a period of 17 minutes, a solution of 1.8 g diethyl azodicarboxylate in 5 mL of dry tetrahydrofuran, keeping the temperature at 0°. The mixture was stirred at room temperature for 6 hours and the solvent was removed under vacuum. The residue was stirred with 25 mL of toluene and 25 mL of ether first at room temperature, then in an ice bath for 15 min. The solids were removed by filtration and the filtrate was concentrated. Further purification of the residue was best achieved by chromotography on silica and elution with ethyl acetate/triethylamine (98:2). The free base of the title compound had the following NMR spectrum (in CDCl$_3$): δ7.8 (m, 2H); 7.7 (m, 2H) 7.2–7.3 (m, 5H); 5.6 (t, 1H); 4.2 (s, 2H), 3.0 (narrow m, 2H), 2.8 (m, 2H); 2.6 (m, 4H); 2.2 (m, 2H) . The 2: 1 fumarate had mp 170°–174° (dec).

Anal. Calcd. for C$_{24}$H$_{24}$N$_2$O$_4$: C, 71.27; H, 5.98; N, 6.93. Found: C, 71.03; H, 6.07; N, 7.17.

The starting material, 1-(2-phenylethyl) -1,2,3,6-tetrahydro- 4-pyridinemethanol, was prepared as follows.

A mixture of 10.9 g of 4-pyridinemethanol, 25 g of 2-bromoethylbenzene an 30 mL of dimethylformamide was stirred in a 90° oil bath for 3 hours. Removal of the solvent and crystallization of the residue from 30 mL of ethanol gave 23.4 g (80%) of 1-(2-phenylethyl)-4-hydroxymethylpyridinium bromide, mp 132°–134°. NMR (DMSO) δ8.9 (d, 2H): 8.0 (d, 2H); 7.2–7.4 (m, 5H); 6.0 (t, 1H), 4.8–4.9 (d+t, 4H); 3.3 (t, 2H).

To a mixture of 16.0 g of the above product and 160 mL of ethanol was added, at 0°, 6.0 g of sodium borohydride over a period of 20 minutes, keeping the temperature below 5°. The mixture was stirred in an ice bath for 30 minutes and 80 mL of 10% hydrochloride acid was added below 0°. The mixture was made basic with 15% sodium hydroxide after stirring at room temperature for 1 hour, and the product was extracted into methylene chloride. Removal of the solvent from the extracts and short-path distillation of the residue (to 170° bath temperature, 1 micron) gave 7.89 g ( 67% ) of 1-(2-phenylethyl)- 1,2,3,6-tetrahydro-4-pyridinemethonol. NMR (CDCl$_3$) δ7.2–7.3 (m, 5H); 5.6 (t, 1H); 4.0 (m, 2H); 3.0 (m, 2H); 2.8 (m, 2H); 2.7 (m, 4H); 2.0–2.2 (m, 2H).

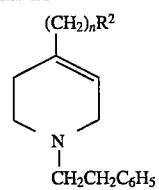

TABLE 6 / TABLE 6-continued

| Ex. # | R$^2$ | n | m.p. (°C.) |
|---|---|---|---|
| 114 | phthalimido | 1 | 170–174 (dec)[b] |
| 115 | phthalimido | 2 | 216–217[a] |
| 116 | phthalimido | 3 | 137–138[b] |
| 117 | cis-4-cyclohexene-1,2-dicarboximido | 1 | 238–240[a] |
| 118 | cis-4-cyclohexene-1,2-dicarboximido | 3 | 184–185[a] |
| 119 | cis-cyclohexane-1,2-dicarboximido | 1 | 172–173[b] |
| 120 | cis-cyclohexane-1,2-dicarboximido | 2 | 195–196[b] |
| 121 | cis-cyclohexane-1,2-dicarboximido | 3 | 202–203[a] |

TABLE 6-continued

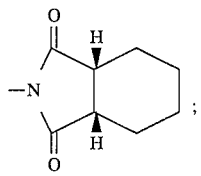

| Ex. # | R² | n | m.p. (°C.) |
|-------|-----|---|-----------|

ªHCl salt
ᵇFumarate

EXAMPLE 122

2-[1-(2-Phenylethyl)-4-phenyl-4
-piperidine-methyl]-cis- 3a; 4, 5, 6, 7,
7a-hexalydro-1H-isoindole-1,3(2H)-dione $R^1$=CH₂CH₂Ph; n=1; $R^2$=

$R^{16}$=Ph; chain attached to C-4 of the piperidine).

A mixture of 0.67 g (2.3 mmoles) of 1-(2-phenylethyl)-4-phenyl-4-piperidinemethylamine, 0.70 g (4.5 mmole) of cis-1,2-cyclohexanedicarboxylic anhydride and 2 mL of dimethylformamide was heated under reflux for 8 hours. The solvent was removed and the residue was dissolved in toluene. The solution was stirred with 10% aqueous sodium carbonate solution, the layers were separated and the aqueous layer was extracted with tolueue. Concentration of the dried toluene layers gave 0.85 g (87%) of the title compound. NMR (CDCl₃) δ7.0–7.4 (m, 10H); 3.6 (s, 2H) and 1.2–2.8 (m, 22H). The fumaric acid salt had mp 220°–221° (dec.) after crystallization from 90% aqueous 1-propanol.

Anal. Calcd. for $C_{32}H_{38}N_2O_6$: C, 70.31; H, 7.01; N, 5.12. Found: C, 70.05; H, 6.99; N, 5.04.

The starting material, 1-(2-phenylethyl)-4-phenyl- 4-piperidinemethylamine, was prepared as follows.

To a solution of 20.0 g (95 mmoles) of N-(2-phenylethyl)diethanolamine in 40 mL of chloroform was added, over a period of 1 hour, 20 mL of thionyl chloride in 20 mL of chloroform. The mixture was heated under reflux for 2 hours and concentrated to give N-(2-phenylethyl)-N,N-bis(2-chloroethyl)amine hydrochloride as an oil. NMR (CDCl₃) δ7.2–7.4 (m, 5H); 4.1 (t, 4H); 3.6 (t, 4H); 3.5 (m, 2H) and 3.2 (m, 2H).

A mixture of 4.25 g (15 mmoles) of the above hydrochloride, 25 mL of 50% aqueous sodium hydroxide solution, 2.0 g (17 moles) of benzyl cyanide and 0.5 g of hexadecyltributylphosphonium bromide was stirred for 30 minutes and then heated in 100° oil bath, with stirring, for 1 hour. The cooled mixture was washed with 25 mL of water and extracted with toluene. The extracts were stirred with 20 mL of 10% hydrochloric acid and precipitate was collected by filtration, washed with toluene and water, and made basic with sodium hydroxide. Extraction with methylene chloride, removal of the solvent from the dried extracts, and short-path distillation of the residue (175°–210° bath temperature, 1 micron) gave 2.19 g (50%) of 1-(2-phenylethyl)-4-phenyl-4-piperidinecarbonitrile, NMR (CDCl₃) δ7.2–7.6 (m, 10H); 3.2 (d, 2H); 2.9 (m, 2H); 2.8 (m, 2H); 2.6 (m, 2H) and 2.2 (m, 4H).

To a solution of 2.18 g (7.5 mmoles) of the above compound in 5 mL of toluene was added with cooling 5 mL (17 mmoles) of sodium bis(2-methoxyethoxy)aluminum hydrdile in toluene. The mixture was stirred for 1 hour and then heated, with stirring, in a 60° oil bath for one hour. Aqueous sodium hydroxide (15 mL) was added with cooling, and the mixture was extracted with toluene. Removal of the solvent from the dried extracts and short-path distillation of the residue (165°–190° bath temperature, 2, micron) gave 2.00g (91%) of 1-(2-phenylethyl)- 4-phenyl-4-piperidinemethylamine. NMR (CDCl₃) δ7.1–7.4 (m, 10H), 2.7–2.8 (m, 6H); 2.5 (m, 2H); 2.3 (m, 4H); 1.8 (t, split further, 2H) and 1.3 (br, 2H).

TABLE 7

| Ex # | R² | R¹⁶ | m.p. (°C.) |
|------|-----|------|-----------|
| 122 | (cyclohexane-fused dione) | Ph | 221–222 (dec) |
| 123 | (cyclohexane-fused dione) | 3-ClC₆H₄ | 221–222 (dec) |
| 124 | (cyclohexane-fused dione) | 4-ClC₆H₄ | 217–218 (dec) |
| 125 | (cyclohexane-fused dione) | 3-MeOC₆H₄ | 217–218 (dec) |

TABLE 7-continued

[Structure: R16 and R2 substituted piperidine with N-CH2CH2Ph, and fumaric acid (HO2C-CH=CH-CO2H)]

| Ex # | R² | R¹⁶ | m.p. (°C.) |
|---|---|---|---|
| 126 | [hexahydroisoindole-1,3-dione, cis-fused H's] | 3-CF₃C₆H₄ | 214–215 (dec) |
| 127 | [hexahydroisoindole-1,3-dione, cis-fused H's] | 1-naphthyl | 220–222 (dec) |
| 128 | [hexahydroisoindole-1,3-dione, cis-fused H's] | 3-thienyl | 208–212 (dec) |
| 129 | [hexahydroisoindole-1,3-dione, cis-fused H's] | benzothiophen-3-yl | 222–223 (dec) |
| 130 | [phthalimide] | 3-ClC₆H₄ᵃ | 277 |
| 131 | [bicyclic imide with bridge] | 3-ClC₆H₄ | 253 (dec) |

ᵃHCl salt

EXAMPLE 132

2-[1-(2-Phenylethyl)-4-(4-methyl)piperidinylmethyl]-cis-3a,4,5,6,7,7a-hexahydro-1H-isoindole-1,3(2H)-dione Method B $R^1$=CH$_2$CH$_2$Ph; $R^{16}$=CH$_3$; n=1; $R^2$=

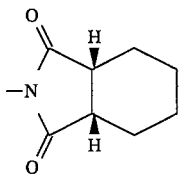

To 0.44 g (1.9 mmol) of 1-(2-phenylethyl)-4-methyl-4-aminomethylpiperidine was added 5 mL of DMF and 0.29 g (1.9 mmol) of cis-1,2-cyclohexanedicarboxylic anhydride. The mixture was refluxed for 4 hours, diluted with water and extracted with ethyl acetate. The combined organic extracts were washed with saturated sodium bicarbonate solution and saturated sodium chloride solution, dried and evaporated to give 0.51 g (73% yield) of the title compound as a yellow oil.

The fumaric acid salt had m.p. 185° after crystallization from 2-propanol; NMR (DMSO-d$_6$): δ7.17–7.45 (m, 5H); 6.58 (s, 2H); 3.27 (s, 2H); 2.71–2.90 (m, 8H); 2.58 (t, 2H); 1.45–1.95 (m, 6H); 1.14–1.42 (m, 6H); 0.94 (s, 3H). Calculated m/e for C$_{16}$H$_{25}$N$_2$O$_2$ (parent ion minus benzyl) 277.1916; found 277.1915.

The starting material, 1-(2-phenylethyl)-4-methyl- 4-aminomethylpiperidine, was prepared as follows:

A mixture of 5.00 g (33 mmol) of ethyl isonicotinate, 6.12 g (33 mmol) of 2-bromoethylbenzene and 25 mL of 2-propanol were heated at reflux for 17 hours. The mixture was evaporated to dryness and triturated 3×75 mL with ether. The excess ether was removed by evaporation and there was obtained 8.91 g of 1-(2-phenylethyl)-4-carboethoxypyridinium bromide as a yellow solid. NMR (CDCl$_3$) δ8.97 (d, 2H); 8.34 (d, 2H); 7.13–7.2 6 (m, 5H); 5.35–5.42 (m, 2H); 4.41–4.50 (q, 2H); 3.39–3.47 (t, 2H); 2.58–2.65 (m, 2H); 1.37–1.46 (t, 3H).

A mixture of 5.90 g ( 17.5 mmol) of 1-(2-phenylethyl)-4-carboethoxypyridinium bromide, 0.60 g of platinum (IV) oxide and 100 mL of methanol was hydrogenated at 50 p.s.i. and room temperature for 1.5 hours. The reaction mixture was filtered, concentrated and the residue dissolved in water. The aqueous solution was made alkaline to pH 9–10 with aqueous potassium carbonate and extracted with ethyl acetate. The organic extracts were washed with saturated sodium bicarbonate solution, saturated sodium chloride solution, dried and evaporated to afford 4.11 g of 1-(2-phenylethyl)- 4-carboethoxypiperidine as a yellow oil. NMR (CDCl$_3$) δ7.16–7.32 (m, 5H); 4.08–4.19 (q, 2H); 2.91–3.02 (m, 2H); 2.77–2.88 (m, 2H); 2.53–2.65 (m, 2H); 2.23–2.35 (m, 1H); 2.03–2.15 (m, 2H); 1.87–1.98 (m, 2H); 1.72–1.88 (m, 4H); 1.20–1.30 (t,3H).

To 2.64 mL (18.9 mmol) of diisopropylamine in 30 mL of dry THF at −78° was added 6.9 mL (17.3 mmol) of 2.5 M n-butyllithium in hexanes. The mixture was allowed to warm to room temperature and then was cooled once again to −78°. To the stirred solution was added 4.11 g (15.7 mmol) of 1-(2-phenylethyl)-4-carboethoxypiperidine in 25 mL of dry THF. The mixture was allowed to warm to −40° and 0.98 mL (15.7 mmol) of iodomethane was added to the reaction mixture. The mixture was stirred at −40° for 15 minutes and then allowed to stir at room temperature for 3 hours. The mixture was evaporated to dryness and the residue was dissolved in water. The aqueous solution was extracted with methylene chloride and the extracts were dried and evaporated to give 3.70 g of 1-( 2-phenylethyl)-4-methyl-4-carboethoxypiperidine as a yellow oil. NMR (CDCl$_3$) δ7.15–7.21 (m, 5H); 4.11–4.20 (q, 4H); 2.71–2.94 (m, 4H): 2.52–2.61 (m, 2H): 2.11–2.24 (m, 4H); 1.47–1.59 (m, 2H); 1.21–1.30 (t, 3H); 1.20 (s, 3H).

To a suspension of 0.51 g (13.4 mmol) of lithium aluminum hydride in 20 mL of THF under nitrogen was added dropwise a solution of 3.70 g (13.4 mmol) of 1-(2-phenylethyl)- 4-methyl-4-carboethoxypiperidine in 15 mL of THF. The solution was heated at reflux for 3 hours. To the cooled reaction mixture (ice bath) was slowly added 0.5 mL of water, followed by 0.5 mL of 15% sodium hydroxide followed by 1.5 mL of water. The precipitated lithium salts were removed by filtration. The filtrate was evaporated to dryness. The residue was reconstituted in methylene chloride, washed with a small amount of water, dried and evaporated to afford 2.97 g of 1-(2-phenylethyl)-4-methyl-4-hydroxymethyl-piperidine as a yellow oil. NMR (CDCl$_3$) δ7.16–7.23 (m, 5H); 3.40 (s, 2H); 2.79–2.87 (m, 2H); 2.57–2.71 (m, 4H); 2.31–2.42 (m, 2H); 1.57–1.63 (m, 5H); 0.97 (s, 3H).

A solution of 10 mL of methylene chloride and 0.4 mL (4.4 mmol) of oxalyl chloride was cooled under nitrogen to −60°. A solution of 0.68 mL of dimethylsulfoxide in 2 mL of methylene chloride was added dropwise to the solution. After stirring for 2 minutes 0.95 g (4 mmol) of 1-(2-phenylethyl)-4-methyl-4-hydroxymethyl-piperidine was added in 2–3 mL of methylene chloride. Stirring was continued for an additional 15 minutes. Triethylamine (2.8 mL, 20 mmol) was added to the reaction mixture and stirring was continued for 5 min, then the mixture was allowed to warm to room temperature. Water (20 mL) was added and the aqueous mixture was extracted with methylene chloride. The organic extracts were washed with brine, dried and evaporated to give 1-(2-phenylethyl)-4-methyl- 4-formyl-piperidine as a clear oil in quantitative yield. NMR (CDCl$_3$) δ9.46 (s, 1H); 7.16–7.27 (m, 5H); 2.84–3.00 (br, 1H); 2.75–2.82 (m, 2H); 2.65–2.75 (m, 2H); 2.55–2.63 (m, 2H); 2.27 (t, 2H); 1.98–2.09 (m, 2H); 1.51–1.63 (m, 2H); 1.05 (s, 3H).

To 0.40 g (6.1 mmol) of potassium hydroxide in 3 mL of water was added 0.42 g (6.1 mmol) of hydroxylamine hydrochloride. After stirring for 5 minutes at room temperature, a solution of 0.94 (4.1 mmol) of 1-(2-phenylethyl)-4-methyl-4-formylpiperidine in 20 mL of 2-propanol was added. The reaction was refluxed for 4 hours. The mixture was evaporated to dryness and the residue dissolved in 10 mL of water. The aqueous mixture was extracted with methylene chloride. The organic extracts were dried and evaporated to give 0.85 g of the oxime as a clear oil. The oxime was chromatographed on silica gel using chloroform:methanol (95:5) to elute. There was recovered 0.58 g of 1-(2-phenylethyl)- 4-methyl-4-oximinomethyl-piperidine as a white solid. NMR (CDCl$_3$) δ7.28 (s, 1H); 7.17–7.24 (m, 5H); 2.80–2.84 (t, 2H); 2.48–2.70 (m, 6H); 1.88–2.00 (m, 2H); 1.58–1.65 (m, 2H); 1.11 (s, 3H).

A mixture containing 0.58 g (2.4 mmol) of 1-(2-phenylethyl)- 4-methyl-4-4-oximinomethylpiperidine, 100 mL of methanol, 80 mg of platinum (IV) oxide and 0.75 mL of concentrated hydrochloric acid was hydrogenated at 40 p.s.i. for 2 hours. The mixture was filtered and evaporated. The residue was dissolved in water and made alkaline with aqueous potassium carbonate. The aqueous mixture was extracted with methylene chloride. The organic extracts are dried and evaporated to give 0.44 g of 1-(2-phenylethyl)-4-methyl-4-aminomethylpiperidine. NMR (CDCl$_3$) δ7.18–7.28 (m, 5H); 5.22–5.45 (br, 2H); 2.89 (s, 2H); 2.78–2.88 (m, 2H); 2.55–2.67 (m, 2H); 2.19 (t, 2H); 1.51–1.78 (m, 4H); 1.27–1.49 (m, 2H); 0.98 (s, 3H).

TABLE 8

| Ex. # | | m.p. (°C.) |
|---|---|---|
| 132 | [structure] | 185 |
| 133 | [structure] | 220 (dec) |

*fumarate

TABLE 9

[structure with $R^9$, .HCl]

| Ex. # | X | $R^9$ | m.p. (°C.) |
|---|---|---|---|
| 134 | H | $C_6H_5$ | 254–256 |
| 135 | H | $(CH_2)_3CH_3$ | 233–235 |
| 136 | H | $C_6H_4$-4-F | 253–255 |
| 137 | F | $CH_3$ | 242–244 |
| 138 | H | $(CH_2)_5CH_3$ | 204–206 |
| 139 | H | $CH_2CH(CH_3)_2$ | 247 (dec) |
| 140 | H | $CH(CH_3)CH_2CH_3$ | 241 (dec) |
| 141[a] | H | 2-furyl | 197–201 |
| 142 | H | 2-thienyl | 239 (dec) |
| 143 | H | $C_6H_4$-4-$CH_3$ | 218 (dec) |
| 144 | H | $(CH_2)_2CH_3$ | 234 (dec) |

[a]Fumarate salt and 2-PrOH solvate

UTILITY

The compounds of this invention and their pharmaceutically acceptable salts or N-oxides thereof possess psychotropic properties, particularly antipsychotic activity of good duration with selective sigma receptor antagonist activities while lacking the typical movement disorder side-effects of standard dopamine receptor antagonist antipsychotic agents. These compounds may also be useful as antidotes for certain psychotomimetic agents, such as phencyclidine (PCP) and as antidyskinetic agents. The compounds of the present invention may also exhibit serotonin 5HT2 receptor-blocking activity.

In Vitro

Sigma Receptor Binding Assay

Male Hartley guinea pigs (250–300 g, Charles River) were sacrificed by decapitation. Brain membranes were prepared by the method of Tam (Proc. Natl. Acad. Sci. USA 80: 6703–6707, 1983). Whole brains were homogenized (20 sec.) in 10 vol (wt/vol) of ice-cold 0.34 M sucrose with a Brinkmann Polytron (setting 8). The homogenate was centrifuged at 920×g for 10 min. The supernatant was centrifuged at 47,000×g for 20 min. The resulting membrane pellet was resuspended in 10 vol (original wt/vol) of 50 mM Tris HCl (pH 7.4) and incubated at 37° C. for 45 min to degrade and dissociate bound endogenous ligands. The membranes were then centrifuged at 47,000× g for 20 min and resuspended in 50 mM Tris HCl (50 mL per brain).

0.5 mL aliquots of the membrane preparation were incubated with unlabeled drugs, 1 nM (+)—[$^3$H]SKF 10,047 in 50 mM Tris HCl, pH 7.4, in a final volume of 1 mL. Nonspecific binding was measured in the presence of 10 μM (+)—SKF 10,047. The apparent dissociation constant (Kd) for (+)—[$^3$H]SKF 10,047 is 50 nM. After 45 rain of incubation at room temperature, samples were filtered rapidly through Whatman GF/C glass filters under negative pressure, and washed 3 times with ice-cold Tris buffer (5 mL).

$IC_{50}$s were calculated from log-logit plots. Apparent $K_i$s were calculated from the equation, $K_i = IC_{50}/[1+(L/K_d)]$, where L is the concentration of radioligand and $K_d$ is its dissociation constant. Data are shown in Table I (+++, $K_i$ 1–30 nM; ++, K 31–100 nM; +, $K_i$ 101–500 nM; –, $K_i$ >500 nM).

Dopamine Receptor Binding

Membranes were prepared from guinea pig striatum by the method described for sigma receptor binding. The membranes were then resuspended in 50 mM Tris HCl (9 mL per brain).

0.5 mL aliquots of the membrane preparation were incubated with unlabeled drugs, and 0.15 nM [$^3$H]spiperone in a final volume of 1 mL containing 50 mM Tris HCl, 120 mM NaCl and 1 mM $MgCl_2$ (pH 7.7). Nonspecific binding was measured in the presence of 100 nM (+)-butaclamol After 15 min of incubation at 37° C. samples were filtered rapidly through Whatman GF/C glass filters under negative pressure, and washed three times with ice-cold binding buffer (5 mL). Data are shown in Table I (+++, $K_i$ 1–30 nM; ++, $K_i$ 31–100 nM; +, $K_i$ 101–500 nM; –, $K_i$ >500 nM).

The data in Table I indicate that haloperidol, a typical antipsychotic drug, has potent binding affinity for both the sigma and dopamine receptors. This binding profile of haloperidol reflects the therapeutic activity as well as the motor side effects caused by antagonism of the dopamine receptors. In contrast, the examples of this invention shown in Table I indicate potent and selective binding affinity for sigma receptors without binding to the dopamine receptors. Therefore these compounds are not expected to produce the extrapyramidal symptoms that are typical of that produced by haloperidol and other typical antipsychotics that are dopamine receptor antagonists.

In Vivo

Mescaline-Induced Scratching in Mice

This is a modification of the procedure of Fellows and Cook (in Psychotropic Drugs, ed. by S. Garrattini and V. Ghatti, pp. 397–404, Elsevier, Amsterdam, 1957) and Deegan and Cook (J. Pharmacol. Exp. Ther. 122: 17A, 1958). Male CF1 Mice (Charles River) were injected orally with test compound and placed singly into square (13 cm) Plexiglass observation chambers. Twenty minutes later mice were injected orally with mescaline (25 mg/kg). Beginning 25 minutes after treatment with mescaline (45 minutes after treatment with test compound), scratching episodes were counted during a 5 minute observation period. A scratching episode is defined as a brief (1–2 sec) burst of scratching either the head or the ear with the hind foot. Data are shown in Table II (+++, $ED_{50}$ <11 mg/kg p.o.; ++, $ED_{50}$ 11–20 mg/kg p.o.; +, $ED_{50}$ 21–70 mg/kg p.o.; –, $ED_{50}$ >70 mg/kg p.o.).

Isolation-Induced Aggression in Mice

This is a modification of the method of Yen et al. (Arch. Int. Pharmacodyn. 123: 179–185, 1959) and Jannsen et al. (J. Pharmacol. Exp. Ther. 129: 471–475, 1960). Male Balb/c mice (Charles River) were used. After 2 weeks of isolation in plastic cages (11.5×5.75×6 in) the mice were selected for aggression by placing a normal group-housed mouse in the cage with the isolate for a maximum of 3 min. Isolated mice failing to consistently attack an intruder were eliminated from the colony.

Drug testing was carried out by treating the isolated mice with test drugs or standards. Fifteen min after dosing with drugs by the oral route (p.o.), one isolated mouse was removed from its home cage and placed in the home cage of another isolate. Scoring was a yes or no response for each pair. A maximum of 3 min was allowed for an attack and the pair was separated immediately upon an attack. Selection of home cage and intruder mice was randomized for each test. Mice were treated and tested twice a week with at least a 2 day washout period between treatments. Data are shown in Table II (+++, $ED_{50}$ <11 mg/kg p.o.; ++, $ED_{50}$ 11–20 mg/kg p.o.; +, $ED_{50}$ 21–70 mg/kg p.o.; –, $ED_{50}$ >70 mg/kg p.o. )

As shown in Table II, haloperidol and Examples 3, 6, 15, 17 and 20A all have potent activities in inhibiting the isolation-induced aggressive behavior indicating psychotropic activities.

PCP-Induced Turning Behavior in Rats

Male Sprague-Dawley rats (CD/CR, Charles River), weighing 190–290 g, were used for surgery. In order to spare nonadrenergic neurons, rats were injected with 25 mg/kg imipramine intraperitoneal (i.p.) 30 min before surgery. The rats were anesthetized with a 1:1.2 ratio mixture of Xylazine:Ketamine given 0.1 mL/100 g body weight intramuscular (i.m.). A Ringers-Wydaze (100:0.01) solution was given to prevent dehydration. Dopamine was depleted in the right striatum by injecting the neurotoxin 6-hydroxydopamine (6-OHDA) into the substantia nigra of the right cerebral hemisphere. Five mg of 6-OHDA was dissolved in 5 mL of a 0.04% ascorbic acid solution which had been deoxygenated with nitrogen. Five µL of the 6-OHDA solution was injected into the substantia nigra through a 26 gauge needle over a five min period. Stereotaxic injection coordinates were −2.5 mm posterior to bregma, −2.1 mm right of the midsagittal suture, and −8.6 mm below the skull surface with the incisor bar set at +5.0 mm. Following surgery they were given 10 days to recover while housed four per cage (45.0 L×20.0 H×26.0 W) with ALPHA-dri bedding and ad lib access to Pro-Lab rodent chow and deionized water. Following recovery, the wood clips were removed, the rats were individually housed in suspended cages, and they were placed on a restricted diet so that their weight did not exceed 375 g. At all times they were housed in the animal care facility under a 12—12 hour light/dark cycle (light on at 6:00 h, light off at 18:00 h).

Rotation rate and direction were determined with Coulbourn Instruments Rotometry Monitors. Clockwise and counter clockwise rotations were recorded at 30 and 60 min intervals. The rats were examined for correct lesion location by testing for rotational activity induced by subcutaneous (s.c.) injections of 3.0 mg/kg D-amphetamine $SO_4$, and 2.0 mg/kg PCP HCl, respectively. These drugs were administered in the following sequence: Amphetamine was given 30 sec before testing. Seven days later, the rats were injected with PCP 30 sec before testing. Only those rats with an ipsilateral rotation rate of 2.5 turns per min or higher were used in subsequent tests.

Methocel® or test drugs were administered p.o. 20 min before testing. Phencyclidine (1.5 mg/kg) was given s.c. immediately before testing.

The data was analyzed with an analysis of variance statistical test, and individual comparisons of each dose of test drug to control were made with Dunnett's multiple range test. The $ED_{50}$ was calculated with a Litchfield and Wilcoxon test using percent of control values. Data are shown in Table III (+++, $ED_{50}$ <11 mg/kg p.o.; ++, $ED_{50}$ 11–20 mg/kg p.o.; +, $ED_{50}$ 21–70 mg/kg p.o.; −, $ED_{50}$ >70 mg/kg p.o.).

Induction of Catalepsy

This is a modification of the method of Costall and Naylor (Psychopharmacologia (Berl.), 43, 69–74, 1975). Male CD rats (Charles River) weighing 250–300 g were treated with test drugs and standards and tested for the presence of catalepsy 30 min, 60 min, and 90 min after treatment. To test for catalepsy, each rat is placed with its front paws over a 10 cm high horizontal bar. The intensity of catalepsy is measured by the length of time it takes the animal to move both forelegs to the table. A time of 20 sec is considered maximal catalepsy. Data are shown in Table III.

As shown in Table III, both haloperidol and Example 3 have potent activity in inhibiting the potent hallucinogen PCP-induced turning behavior in rats, supporting their use for treatment of psychosis. In the catalepsy test which is a model for extrapyramidal symptoms, haloperidol is very potent in producing catalepsy and this agrees well with the side-effect profile of haloperidol in the clinic. In contrast, Example 3 does not produce catalepsy and suggests very low potential for extrapyramidal symptoms and tardive dyskinesia. Data are shown in Table III (+++, $ED_{50}$ <11 mg/kg p.o.; ++, $ED_{50}$ 11–20 mg/kg p.o.; +, $ED_{50}$ 21–70 mg/kg p.o.; −, $ED_{50}$>70 mg/kg p.o.).

TABLE I

In vitro Receptor Binding Affinity

| Example | Sigma | Dopamine (D-2) |
|---|---|---|
| haloperidol | +++ | +++ |
| 1 | ++ | − |
| 2 | ++ | − |
| 3 | +++ | − |
| 4 | +++ | − |
| 5 | + | − |
| 6 | ++ | − |
| 7 | + | − |
| 12 | +++ | − |
| 13 | ++ | − |
| 14 | +++ | − |
| 15 | +++ | − |
| 16 | ++ | − |
| 17 | +++ | − |
| 18 | ++ | − |
| 19 | + | + |
| 20 | +++ | − |
| 21 | + | − |
| 22 | ++ | − |
| 23 | +++ | − |
| 24 | +++ | − |
| 34 | +++ | − |
| 35 | ++ | − |
| 36 | +++ | − |
| 37 | + | − |
| 38 | +++ | − |
| 39 | +++ | − |
| 40 | +++ | − |
| 41 | +++ | − |
| 42 | +++ | − |
| 43 | +++ | − |
| 44 | +++ | − |
| 47 | +++ | − |
| 48 | +++ | − |
| 49 | +++ | − |
| 50 | ++ | − |
| 52 | +++ | − |
| 53 | +++ | + |
| 54 | ++ | − |
| 55 | ++ | − |
| 56 | +++ | − |
| 57 | +++ | − |
| 58 | +++ | − |
| 59 | ++ | − |
| 61 | +++ | − |
| 62 | +++ | − |
| 63 | − | − |
| 9 | +++ | + |
| 10 | +++ | ++ |
| 8 | + | − |
| 25 | + | + |
| 26 | +++ | − |
| 27 | +++ | − |
| 28 | +++ | − |
| 29 | ++ | − |
| 30 | +++ | + |
| 31 | + | − |
| 32 | + | − |
| 33 | +++ | − |
| 64 | ++ | − |
| 65 | ++ | + |
| 66 | ++ | − |
| 67 | + | − |
| 68 | + | − |
| 69 | +++ | − |
| 70 | + | + |
| 71 | +++ | − |
| 72 | +++ | + |
| 73 | ++ | − |

TABLE I-continued

| | In vitro Receptor Binding Affinity | |
|---|---|---|
| Example | Sigma | Dopamine (D-2) |
| 86 | + | + |
| 113 | ++ | − |
| 115 | +++ | − |
| 116 | ++ | − |
| 117 | +++ | − |
| 118 | +++ | − |
| 119 | +++ | − |
| 120 | +++ | − |
| 121 | +++ | − |
| 74 | + | − |
| 75 | +++ | − |
| 76 | ++ | − |
| 77 | ++ | − |
| 122 | +++ | − |
| 123 | +++ | − |
| 124 | +++ | − |
| 125 | ++ | − |
| 126 | +++ | − |
| 127 | ++ | − |
| 128 | +++ | − |
| 129 | +++ | + |
| 130 | +++ | − |
| 131 | ++ | − |
| 132 | +++ | − |
| 133 | +++ | − |
| 134 | ++ | |
| 136 | ++ | |
| 138 | +++ | |
| 139 | +++ | |
| 140 | ++ | |
| 141 | +++ | |
| 142 | +++ | |

TABLE II

| Example | Inhibition of Isolation-induced Aggression | Mescaline Scratch (10 mg/kg po) |
|---|---|---|
| Haloperidol | +++ | |
| 3 | ++ | |
| 6 | + | |
| 23 | + | |
| 34 | ++ | |
| 39 | + | |
| 134 | | +++ |
| 135 | +++ | +++ |
| 136 | +++ | +++ |
| 137 | +++ | +++ |
| 138 | +++ | +++ |
| 139 | +++ | +++ |
| 140 | | +++ |
| 141 | | +++ |
| 142 | | +++ |
| 143 | +++ | +++ |
| 144 | +++ | +++ |

TABLE III

| | In vivo | |
|---|---|---|
| Example | Inhibition of PCP-induced Turning | Catalepsy |
| Haloperidol | +++ | +++ |
| 3 | + | − |

Dosage and Formulation

The antipsychotic compounds of this invention can be administered as treatment for psychosis or dyskinesia by any means that produces contact of the active agent with the agent's site of action, the sigma receptor, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams per kilogram of body weight, with the preferred dose being 0.1 to about 30 mg/kg. Daily dosage may range from about 1 mg to 2000 mg.

Dosage forms (compositions suitable for administration contain from about 1 milligram to about 100 milligrams of active ingredient per unit. In these pharmaceutical compositions the active ingredient will ordinarily-be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention car be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

What is claimed is:

1. A compound having the formula:

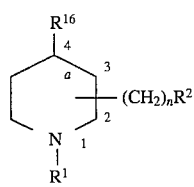

(I)

or a pharmaceutically acceptable salt or an N-oxide thereof wherein:

a is a single or double bond, provided that when a is a double bond, $R^2(CH_2)_n$ is attached at the C-4 position of the piperidine ring and $R^{16}$ is not present;

n is 1–4, provided that when $(CH_2)_nR^2$ is attached to the C-2 position of the piperidine ring then n is 2–4;

$R^1$ is $(CH_2)_mR^3$ or $(CH_2)_pAr$, where m is 1–4 and p is 1–4;

$R^2$ is

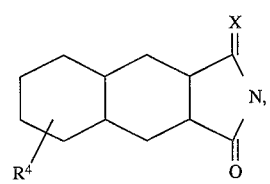

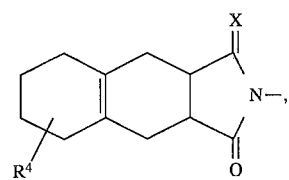

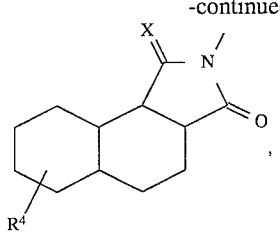

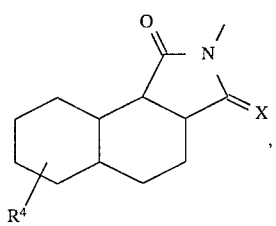

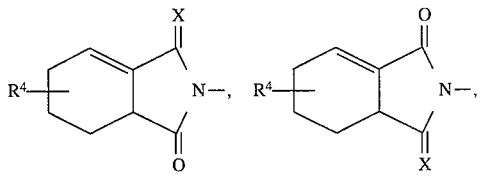

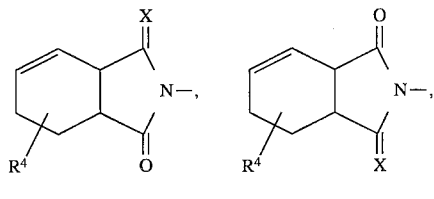

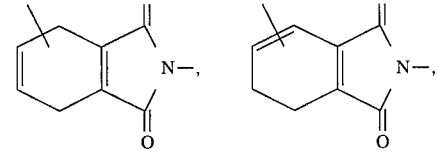

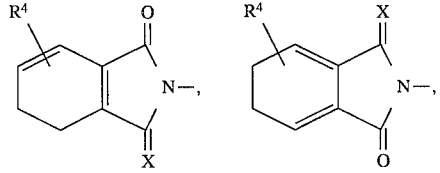

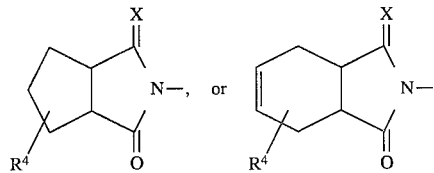

$R^3$ is cycloalkyl of 3 to 8 carbon atoms;

$R^4$ is 1–4 substituents independently selected from the group consisting of H, halogen, $NO_2$, $NH_2$, haloalkyl of 1 to 3 carbon atoms and 1 to 7 halogen atoms, $C_1$–$C_3$ alkyl, $NHCOR^7$, NHCO-phenyl, OH, $OR^8$ and Ar';

$R^7$ and $R^8$ independently are H or alkyl of 1 to 3 carbon atoms;

X is O; (H, H); (H, OH); ($R^9$, OH); (Ar''', OH); (H, $R^9$); or (H, $OR^{10}$);

Ar, Ar', Ar" and Ar'" independently are phenyl, naphthyl, each optionally substituted with 1–5 substituents independently selected from the group consisting of:
H, halogen, OH, alkoxy of 1 to 3 carbon atoms, $NR^{11}R^{12}$, SH, $S(O)_tR^{13}$, where t is 0–2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, or phenyl;

$R^9$ is selected from the group consisting of:
alkyl of 1–20 carbon atoms or alkenyl or alkynyl of 2–20 carbon atoms, said alkyl, alkenyl, or alkynyl group being optionally substituted with substituents independently selected from:
1–2 cycloalkyl groups of 3–8 carbons, 1–6 halogen, 1–3 OH, 1–3 $OR^{10}$, 1–2 Ar""; cycloalkyl of 3–8 carbon atoms; or Ar"";

$R^{10}$ is alkyl of 1–3 carbon atoms;

Ar"" is phenyl, naphthyl, pyrrolyl, furyl, thienyl, indolyl, benzofuryl, benzothienyl, pyridyl, pyrimidyl, quinolyl, or isoquinolyl, each of which may be substituted with 0–5 groups independently selected from the group consisting of:
H, halogen, OH, alkoxy of 1 to 3 carbon atoms, $NR^{11}R^{12}$, SH, $S(O)_tR^{13}$, where t is 0–2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, or phenyl;

$R^{11}$, $R^{12}$, $R^{13}$, $R^{14}$, and $R^{15}$ independently are H or alkyl of 1 to 3 carbon atoms; and $R^{16}$ is H; alkyl of 1–12 carbons; 2- and 3- thienyl; or phenyl or 1- and 2- naphthyl said phenyl or naphthyl being optionally substituted with one or two substituents independently selected from the group consisting of: F, Cl, Br, I, alkyl, perfluoroalkyl, alkoxy;

with the proviso that when a is a single bond and $(CH_2)_nR^2$ is attached at the 4 position of the piperidine ring, then $R^{16}$ is not 2- and 3- thienyl.

2. A compound of claim 1 wherein $R^1$ is $(CH_2)_pAr$.

3. A compound having the formula:

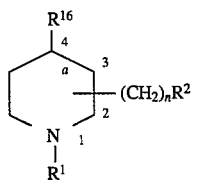
(I)

or a pharmaceutically acceptable salt or an N-oxide thereof wherein;

a is a single or double bond, provided that when a is a double bond, $R^2(CH_2)_n$ is attached at the C-4 position of the piperidine ring and $R^{16}$ is not present;

n is 1–4, provided that when $(CH_2)_nR^2$ is attached to the C-2 position of the piperidine ring then n is 2–4;

$R^1$ is $(CH_2)_mR^3$ or $(CH_2)_pAr$, where m is 1–4 and p is 1–4;

$R^2$ is selected from the group consisting of

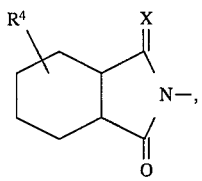 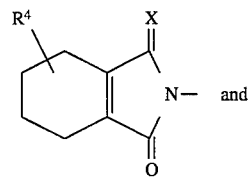

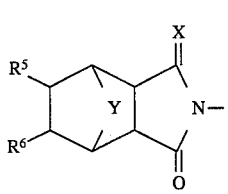

$R^3$ is cycloalkyl of 3 to 8 carbon atoms;

$R^4$ is 1–4 substituents independently selected from the group consisting of H, halogen, $NO_2$, $NH_2$, haloalkyl of 1 to 3 carbon atoms and 1 to 7 halogen atoms, $C_1$–$C_3$ alkyl, $NHCOR^7$, NHCO-phenyl, OH, $OR^8$ and Ar';

$R^5$ and $R^6$ independently are H, alkyl of 1 to 3 carbon atoms, A" or taken together form a 2–5 carbon atom alkyl or alkenyl group;

$R^7$ and $R^8$ independently are H or alkyl of 1 to 3 carbon atoms;

X is O, (H, H); (H, OH); ($R^9$, OH); (Ar'", OH); (H, $R^9$); or (H, $OR^{10}$);

Y is $CH_2$, $CHR^{10}$; $C(R^{10})_2$, $CH_2CH_2$, $(CH_2)_3$,

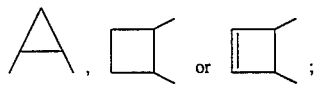;

Ar, Ar', Ar'" and Ar'" independent are phenyl, naphthyl, each optionally substituted with 1–5 substituents independently selected from the group consisting of:
H, halogen, OH, alkoxy of 1 to 3 carbon atoms, $NR^{11}R^{12}$, SH, $S(O)_tR^{13}$, where t is 0–2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, or phenyl;

$R^9$ is selected from the group consisting of:
alkyl of 1–20 carbon atoms or alkenyl or alkynyl of 2–20 carbon atoms, said alkyl, alkenyl, or alkynyl group being optionally substituted with substituents independently selected from:
1–2 cycloalkyl groups of 3–8 carbons, 1–6 halogen, 1–3 OH, 1–3 $OR^{10}$, 1–2 Ar"", cycloalkyl of 3–8 carbon atoms; or Ar"";

$R^{10}$ is alkyl of 1–3 carbon atoms;

Ar"" is phenyl, naphthyl, pyrrolyl, furyl, thienyl, indolyl, benzofuryl, benzothienyl, pyridyl, pyrimidyl, quinolyl, or isoquinolyl, each of which may be substituted with 0–5 groups independently selected from the group consisting of:
H, halogen, OH, alkoxy or 1 to 3 carbon atoms, $NR^{11}R^{12}$, SH, $S(O)_tR^{13}$, where t is 0–2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, or phenyl;

$R^{11}$, $R^{12}$, $R^{13}$, $R^{14}$, and $R^{15}$ independently are H or alkyl of 1 to 3 carbon atoms; and $R^{16}$ is H; alkyl of 1–12 carbons; 2- and 3- thienyl; or phenyl or 1- and 2- naphthyl said phenyl or naphthyl being optionally substituted with one or two substituents independently selected from the group consisting of: F, Cl, Br, I, alkyl, perfluoroalkyl, alkoxy;

with the proviso that when a is a single bond and $(CH_2)_nR^2$ is attached at the 4 position of the piperidine ring, then $R^{16}$ is not 2- and 3- thienyl.

4. A compound of claim 1 wherein $(CH_2)_nR^2$ is attached at the C-4 position of the piperidine ring.

5. A compound of claim 1 wherein X is O, (H, H) or (H, $R^9$) and $R^9$ is alkyl of 1–8 carbon atoms.

6. A compound of claim 1 wherein $R^4$, $R^5$ and $R^6$ are all H.

7. A compound of claim 1 wherein p is 1 or 2.

8. A compound of claim 1 wherein:

a is a single bond;

$R^{16}$ is selected from the group consisting of:
H; alkyl of 1–12 carbons; or phenyl or 1- and 2-naphthyl said phenyl or naphthyl being optionally substituted with one or two substituents independently selected from the group consisting of: F, Cl, Br, I, alkyl, perfluoroalkyl, alkoxy;

$R^1$ is $(CH_2)_pAr$;

$(CH_2)_nR^2$ is attached at the C-4 position of the piperidine ring;

n is 1–4;

$R^2$ is selected from the group consisting of:

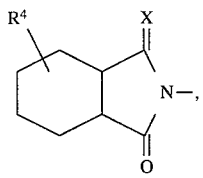 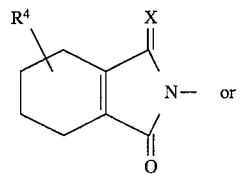 or

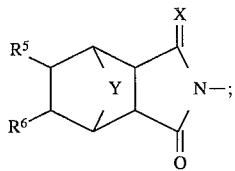

X is O, (H, H), or (H, $R^9$) and $R^9$ is alkyl of 1–8 carbon atoms;

$R^4$, $R^5$ and $R^6$ are all H;

p is 1 or 2;

Ar is phenyl; and

Y is $(CH_2)_3$.

9. A compound of claim 8 which is selected from the following compounds:

(a) a compound wherein:
$R^1$ is $(CH_2)_2$-phenyl;
$(CH_2)_nR^2$ is attached at the C-4 position of the piperidine ring;
n is 1;

$R^2$ is

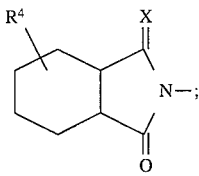

X is O; and
$R^4$ is H;

(b) a compound wherein:
$R^1$ is $(CH_2)_2$-phenyl;
$(CH_2)_nR^2$ is attached at the C-4 position of the piperidine ring;
n is 1;
$R^2$ is

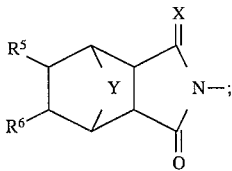

X is O;
Y is $(CH_2)_3$; and
$R^5$ and $R^6$ are H;

(c) a compound wherein:
$R^1$ is $(CH_2)_2$-phenyl;
$(CH_2)_nR^2$ is attached at the C-4 position of the piperidine ring;
n is 1;
$R^2$ is

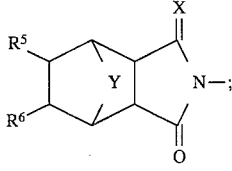

X is O;
Y is O; and
$R^5$ and $R^6$ are H;

(d) a compound wherein:
$R^1$ is $(CH_2)_2$-phenyl;
$(CH_2)_nR^2$ is attached at the C-4 position of the piperidine ring;
n is 1;
$R^2$ is

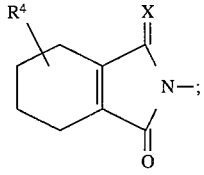

X is (H, H); and
$R^4$ is H;

(e) a compound where in:

R¹ is (CH₂)₂-phenyl;
(CH₂)ₙR² is attached at the C-4 position of the piperidine ring;
n is 1;
R² is

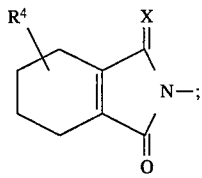

X is (H, CH₃); and
R⁴ is H;

(f) a compound wherein:
R¹ is (CH₂)₂-phenyl;
(CH₂)ₙR² is attached at the C-4 position of the piperidine ring;
n is 1;
R² is

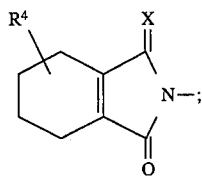

X is (H, n-hexyl); and
R⁴ is H.

10. A compound having the formula:

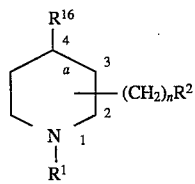
(I)

or a pharmaceutically acceptable salt or an N-oxide thereof wherein:

a is a single or double bond, provided that when a is a double bond, R²(CH₂)ₙ is attached at the C-4 position of the piperidine ring and R¹⁶ is not present;

n is 1–4, provided that when (CH₂)ₙR² is attached to the C-2 position of the piperidine ring then n is 2–4;

R¹ is (CH₂)ₘR³ or (CH₂)ₚAr, where m is 1–4 and p is 1–4;

R² is selected from the group consisting of

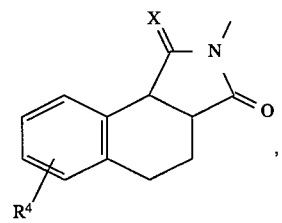

-continued

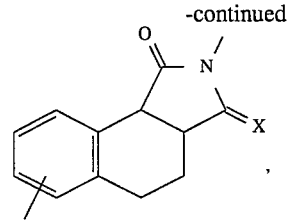

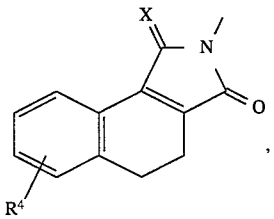

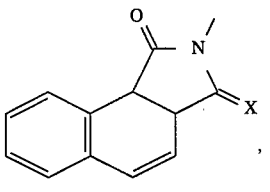

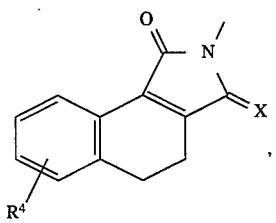

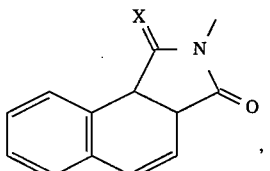

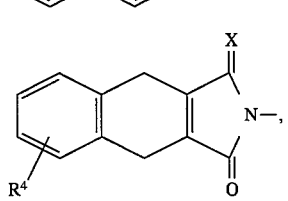

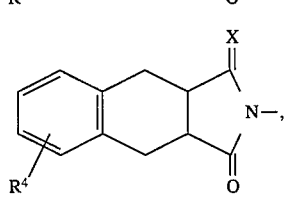

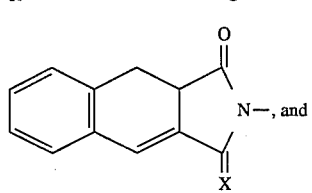

-continued

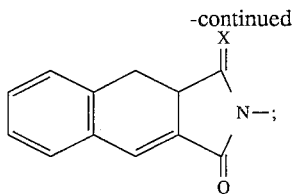

R³ is cycloalkyl of 3 to 8 carbon atoms;

R⁴ is 1–4 substituents independently selected from the group consisting of H, halogen, $NO_2$, $NH_2$, haloalkyl of 1 to 3 carbon atoms and 1 to 7 halogen atoms, $C_1$–$C_3$ alkyl, $NHCOR^7$, NHCO-phenyl, OH, $OR^8$ and Ar';

$R^7$ and $R^8$ independently are H or alkyl of 1 to 3 carbon atoms;

X is O; (H, H); (H, OH); ($R^9$, OH); (Ar''', OH); (H, $R^9$); or (H, $OR^{10}$);

Ar, Ar', Ar'' and Ar''' independently are phenyl, naphthyl, each optionally substituted with 1–5 substituents independently selected from the group consisting of:
  H, halogen, OH, alkoxy of 1 to 3 carbon atoms, $NR^{11}R^{12}$, SH, $S(O)_tR^{13}$, where t is 0–2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, or phenyl;

$R^9$ is selected from the group consisting of:
  alkyl of 1–20 carbon atoms or alkenyl or alkynyl of 2–20 carbon atoms, said alkyl, alkenyl, or alkynyl group being optionally substituted with substituents independently selected from the group consisting of 1–2 cycloalkyl groups of 3–8 carbons, 1–6 halogen, 1–3 OH, 1–3 $OR^{10}$, 1–2 Ar''''; cycloalkyl of 3–8 carbon atoms, and Ar'''';

$R^{10}$ is alkyl of 1–3 carbon atoms;

Ar'''' is phenyl, naphthyl, pyrrolyl, furyl, thienyl, indolyl, benzofuryl, benzothienyl, pyridyl, pyrimidyl, quinolyl, or isoquinolyl, each of which may be substituted with 0–5 groups independently selected from the group consisting of: H, halogen, OH, alkoxy of 1 to 3 carbon atoms, $NR^{11}R^{12}$, SH, $S(O)_tR^{13}$, where t is 0–2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, and phenyl;

$R^{11}$, $R^{12}$, $R^{13}$, $R^{14}$, and $R^{15}$ independently are H or alkyl of 1 to 3 carbon atoms; and $R^{16}$ is H; alkyl of 1–12 carbons; 2- and 3- thienyl; or phenyl or 1- and 2- naphthyl said phenyl or naphthyl being optionally substituted with one or two substituents independently selected from the group consisting of: F, Cl, Br, I, alkyl, perfluoroalkyl, and alkoxy;

with the proviso that when a is a single bond and $(CH_2)_nR^2$ is attached at the 4 position of the piperidine ring, then $R^{16}$ is not 2- and 3- thienyl.

11. A pharmaceutical composition comprising a pharmaceutically acceptable carrier and a therapeutically effective amount of a compound of claim 1.

12. A pharmaceutical composition comprising a pharmaceutically acceptable carrier and a therapeutically effective amount of a compound of claim 2.

13. A pharmaceutical composition comprising a pharmaceutically acceptable carrier and a therapeutically effective amount of a compound of claim 3.

14. A pharmaceutical composition comprising a pharmaceutically acceptable carrier and a therapeutically effective amount of a compound of claim 4.

15. A pharmaceutical composition comprising a pharmaceutically acceptable carrier and a therapeutically effective amount of a compound of claim 5.

16. A pharmaceutical composition comprising a pharmaceutically acceptable carrier and a therapeutically effective amount of a compound of claim 6.

17. A pharmaceutical composition comprising a pharmaceutically acceptable carrier and a therapeutically effective amount of a compound of claim 7.

18. A pharmaceutical composition comprising a pharmaceutically acceptable carrier and a therapeutically effective amount of a compound of claim 8.

19. A pharmaceutical composition comprising a pharmaceutically acceptable carrier and a therapeutically effective amount of a compound of claim 9.

20. A pharmaceutical composition comprising a pharmaceutically acceptable carrier and a therapeutically effective amount of a compound of claim 11.

21. A pharmaceutical composition comprising a pharmaceutically acceptable carrier and a therapeutically effective amount of a compound of claim 10.

* * * * *

UNITED STATES PATENT AND TRADEMARK OFFICE
CERTIFICATE OF CORRECTION

PATENT NO. : 5,480,892

DATED : January 2, 1996

INVENTOR(S) : Engelbert Ciganek, Sang W. Tam, Ann S. Wright

It is certified that error appears in the above-indentified patent and that said Letters Patent is hereby corrected as shown below:

At column 79, line 21, "claim 1" should read --claim 3--.

Signed and Sealed this

Twenty-ninth Day of July, 1997

Attest:

BRUCE LEHMAN

*Attesting Officer*  *Commissioner of Patents and Trademarks*